(12) United States Patent
Jiang et al.

(10) Patent No.: US 8,828,931 B2
(45) Date of Patent: Sep. 9, 2014

(54) BIFUNCTIONAL MOLECULES FOR INHIBITING HIV ENTRY

(75) Inventors: Shibo Jiang, Fresh Meadows, NY (US); Chungen Pan, Guangzhou (CN)

(73) Assignee: New York Blood Center, Inc., New York, NY (US)

( * ) Notice: Subject to any disclaimer, the term of this patent is extended or adjusted under 35 U.S.C. 154(b) by 490 days.

(21) Appl. No.: 12/474,105

(22) Filed: May 28, 2009

(65) Prior Publication Data
US 2009/0298774 A1   Dec. 3, 2009

Related U.S. Application Data

(60) Provisional application No. 61/056,580, filed on May 28, 2008.

(51) Int. Cl.
*C07K 14/16* (2006.01)
*A61K 38/16* (2006.01)
*A61K 38/00* (2006.01)
*C07K 14/005* (2006.01)

(52) U.S. Cl.
CPC .................................. *C07K 14/005* (2013.01); *C12N 2740/16122* (2013.01)
USPC .......................................... 514/3.8; 530/350

(58) Field of Classification Search
CPC .... C07K 14/005; C07K 14/16; C07K 14/162; A61K 38/00; A61K 38/162
See application file for complete search history.

(56) References Cited

U.S. PATENT DOCUMENTS

| | | | |
|---|---|---|---|
| 5,444,044 A | 8/1995 | Jiang et al. | |
| 7,144,991 B2 | 12/2006 | Goshorn et al. | |
| 7,456,251 B2 * | 11/2008 | Dwyer et al. | 530/300 |
| 2002/0094521 A1 * | 7/2002 | Wild et al. | 435/5 |
| 2004/0122214 A1 * | 6/2004 | Bray et al. | 530/350 |

FOREIGN PATENT DOCUMENTS

| | | |
|---|---|---|
| WO | 2004/104033 A2 | 12/2004 |
| WO | 2005/007831 A2 | 1/2005 |
| WO | 2006/105199 A2 | 10/2006 |
| WO | 2008/019817 A1 | 2/2008 |

OTHER PUBLICATIONS

Desplancq et al. Multimerization behavior of single chain Fv variants for the tumour-binding antibody B72.3. Protein Engineering Design and Selection 1994, vol. 7, issue 8, pp. 1027-1033. Abstract only.*
Chan DC Kim PS (1998) HIV entry and its inhibition. Cell 93: 681-684.
Lu M, Blacklow SC, Kim PS (1995) A trimeric structural domain of the HIV-1 transmembrane glycoprotein. Nat Struct Biol 2: 1075-1082.
Chan DC, Fass D, Berger JM, Kim PS (1997) Core structure of gp41 from the HIV envelope glycoprotein. Cell 89: 263-273.
Weissenhorn W et al. (1997) Atomic Structure of the Ectodomain from HIV-1 gp41. Nature 387: 426-428.
Liu S, Wu S, Jiang S (2007) HIV entry inhibitors targeting gp41: from polypeptides to small-molecule compounds. Curr Pharm Des 13: 143-162.
Dervillez X et al. (2006) Stable expression of soluble therapeutic peptides in eukaryotic cells by multimerisation: application to the HIV-1 fusion inhibitory peptide C46. ChemMedChem 1: 330-339.
Jiang S, Lin K, Neurath AR (1991) Enhancement of human immunodeficiency virus type-1 (HIV-1) infection by antisera to peptides from the envelope glycoproteins gp120/gp41. J Exp Med 174: 1557-1563.
Jiang S et al. (2004) N-substituted pyrrole derivatives as novel human immunodeficiency virus type 1 entry inhibitors that interfere with the gp41 six-helix bundle formation and block virus fusion. Antimicrob Agents Chemother 48: 4349-4359.
Neurath AR et al. (2002) Anti-HIV-1 activity of cellulose acetate phthalate: synergy with soluble CD4 and induction of "dead-end" gp41 six-helix bundles. BMC Infect Dis 2: 6.
Chan DC, Chutkowski CT, Kim PS (1998) Evidence that a prominent cavity in the coiled coil of HIV type 1 gp41 is an attractive drug target. Proc Natl Acad Sci USA 95: 15613-15617.
Jiang S, Lin K, Strick N, Neurath AR (1993) HIV-1 inhibition by a peptide. Nature 365: 113.
Lu H, Zhao Q, Xu Z, Jiang S (2003) Automatic quantitation of HIV-1 mediated cell-to-cell fusion with a digital image analysis system (DIAS): application for rapid screening of HIV-1 fusion inhibitors. J Virol Methods 107: 155-161.
Liu S et al. (2005) Different from the HIV fusion inhibitor C34, the anti-HIV drug Fuzeon (T-20) inhibits HIV-1 entry by targeting multiple sites in gp41 and gp120. J Biol Chem 280: 11259-11273.
Liu S et al. (2007) HIV gp41 C-terminal heptad repeat contains multifunctional domains: relation to mechanisms of action of anti-HIV peptides. J Biol Chem 282: 9612-9620.
Reeves JD et al. (2004) Impact of mutations in the coreceptor binding site on human immunodeficiency virus type 1 fusion, infection, and entry inhibitor sensitivity. J Virol 78: 5476-5485.
Bellamy-McIntyre AK et al. (2007) Functional links between the fusion peptide-proximal polar segment and membrane-proximal region of human immunodeficiency virus gp41 in distinct phases of membrane fusion. J Biol Chem 282: 23104-23116.
Wexler-Cohen Y Shai Y (2007) Demonstrating the C-terminal boundary of the HIV 1 fusion conformation in a dynamic ongoing fusion process and implication for fusion inhibition. FASEB J 21: 3677-3684.
Farzan M et al. "Stabilization of human immunodeficiency virus type 1 envelope glycoprotein trimers by disulfide bonds introduced into the gp41 glycoprotein ectodomain." J. Virol. 72:7620-7625, 1998.
Louis JM et al. "Design and Properties of Nccg-gp41, a chimeric pg41 molecule with nanomolar HIV fusion inhibitory activity." J. Biol. Chem. 276:29485-29489, 2001.

(Continued)

*Primary Examiner* — Louise Humphrey
(74) *Attorney, Agent, or Firm* — K&L Gates LLP; Louis C. Cullman; Michelle Glasky Bergman

(57) ABSTRACT

Disclosed herein are bifunctional molecules which inhibit HIV entry into the target cell. Also disclosed are novel anti-HIV therapeutics for treatment of patients infected by HIV, including non-B and multi-drug resistant strains.

16 Claims, 11 Drawing Sheets

(56) References Cited

OTHER PUBLICATIONS

Nelson, JD et al. "Antibody elicited against the pg41 N-heptad repeat (NHR) coiled-coil can neutralize HIV-1 with modest potency but non-neuralizing antibodies also bind to NNR mimetics." Virology 277:170-183, 2008.

Yang X. et al. "Highly stable trimers formed by human immunodeficiency virus type 1 envelope glycoproteins fused with the trimeric motif of T4 bacteriophage fibritin." J. Virol. 76:4634-4642, 2002.

He Y et al. "Identification of a critical motif for the human immunodeficiency virus type 1 (HIV-1) gp41 core structure: implications for designing novel anti-HIV fusion inhibitors." J. Virol. 82:6349-6358, 2008.

Liu S et al. "HIV gp41 C-terminal heptad repeat contains multifunctional domains." J. Bio. Chem. 282:9612-9620, 2007.

Qi Z et al. "Rationally designed anti-HIV peptides containing multifunctional domains as molecule probes for studying the mechanisms of action of the first and second generation HIV fusion inhibitors." J. Bio. Chem. 283:30376-30384, 2008.

Munch et al., "Discovery and Optimization of a Natural HIV-1 Entry Inhibitor Targeting the gp41 Fusion Peptide." Cell, 129, 263-275, Apr. 20, 2007.

Vermeire et al., "Anti-HIV agents targeting the interaction of gp120 with the cellular CD4 receptor." Expert Opin. Investig. Drugs, 14(10): 1199-1212, 2005.

* cited by examiner

SEQUENCE LISTING

```
<160> NUMBER OF SEQ ID NOS: 53

<210> SEQ ID NO 1
<211> LENGTH: 46
<212> TYPE: PRT
<213> ORGANISM: Human immunodeficiency virus

<400> SEQUENCE: 1

Thr Leu Thr Val Gln Ala Arg Gln Leu Leu Ser Gly Ile Val Gln Gln
1               5                   10                  15

Gln Asn Asn Leu Leu Arg Ala Ile Glu Ala Gln Gln His Leu Leu Gln
            20                  25                  30

Leu Thr Val Trp Gly Ile Lys Gln Leu Gln Ala Arg Ile Leu
        35                  40                  45

<210> SEQ ID NO 2
<211> LENGTH: 36
<212> TYPE: PRT
<213> ORGANISM: Human immunodeficiency virus

<400> SEQUENCE: 2

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 3
<211> LENGTH: 38
<212> TYPE: PRT
<213> ORGANISM: Human immunodeficiency virus

<400> SEQUENCE: 3

Thr Thr Trp Met Glu Trp Asp Arg Glu Ile Asn Asn Tyr Thr Ser Leu
1               5                   10                  15

Ile His Ser Leu Ile Glu Glu Ser Gln Asn Gln Gln Glu Lys Asn Glu
            20                  25                  30

Gln Glu Leu Leu Glu Leu
        35

<210> SEQ ID NO 4
<211> LENGTH: 38
<212> TYPE: PRT
<213> ORGANISM: Human immunodeficiency virus

<400> SEQUENCE: 4

Thr Thr Trp Glu Ala Trp Asp Arg Ala Ile Ala Glu Tyr Ala Ala Arg
1               5                   10                  15

Ile Glu Ala Leu Leu Arg Ala Leu Gln Glu Gln Gln Glu Lys Asn Glu
            20                  25                  30

Ala Ala Leu Arg Glu Leu
        35

<210> SEQ ID NO 5
```

<211> LENGTH: 49
<212> TYPE: PRT
<213> ORGANISM: Human immunodeficiency virus

<400> SEQUENCE: 5

Thr Thr Trp Met Ala Trp Asp Arg Glu Ile Asn Asn Tyr Thr Ser Leu
1               5                   10                  15

Ile His Ser Leu Ile Arg Arg Ser Gln Asn Gln Gln Glu Lys Asn Glu
            20                  25                  30

Gln Glu Leu Leu Glu Leu Asp Lys Trp Ala Ser Leu Leu Trp Asn Trp
        35                  40                  45

Phe

<210> SEQ ID NO 6
<211> LENGTH: 123
<212> TYPE: PRT
<213> ORGANISM: Artificial
<220> FEATURE:
<223> OTHER INFORMATION: Bifunctional peptide TLT-1

<400> SEQUENCE: 6

Gly Pro Leu Gly Ser Thr Thr Trp Glu Ala Trp Asp Arg Ala Ile Ala
1               5                   10                  15

Glu Tyr Ala Ala Arg Ile Glu Ala Leu Leu Arg Ala Leu Gln Glu Gln
            20                  25                  30

Gln Glu Lys Asn Glu Ala Ala Leu Arg Glu Leu Gly Gly Gly Gly Ser
        35                  40                  45

Gly Gly Gly Gly Ser Gly Gly Gly Ser Gly Gly Gly Ser Gly
65              70                  75                  80

Ser Leu Ile His Ser Leu Ile Glu Ser Gln Asn Gln Gln Glu Lys
            85                  90                  95

Asn Glu Gln Glu Leu Leu Glu Leu Asp Lys Trp Ala Ser Leu Trp Asn
            100                 105                 110

Trp Phe Tyr Ser Ser Gly Arg Ile Val Thr Asp
        115                 120

<210> SEQ ID NO 7
<211> LENGTH: 123
<212> TYPE: PRT
<213> ORGANISM: Artificial
<220> FEATURE:
<223> OTHER INFORMATION: Bifunctional peptide TLT-2

<400> SEQUENCE: 7

Gly Pro Leu Gly Ser Thr Thr Trp Glu Ala Trp Asp Arg Ala Ile Ala
1               5                   10                  15

Glu Tyr Ala Ala Arg Ile Glu Ala Leu Leu Arg Ala Leu Gln Glu Gln
            20                  25                  30

Gln Glu Lys Asn Glu Ala Ala Leu Arg Glu Leu Gly Gly Gly Gly Ser
        35                  40                  45

Gly Gly Gly Gly Ser Gly Gly Gly Ser Gly Gly Gly Ser Gly
65              70                  75                  80

Ser Leu Ile His Ser Leu Ile Glu Ser Gln Asn Gln Gln Glu Lys
            85                  90                  95

-continued

Asn Glu Gln Glu Leu Leu Glu Leu Asp Lys Trp Ala Ser Leu Trp Asn
                100                 105                 110

Trp Phe Asn Ser Ser Gly Arg Ile Val Thr Asp
        115                 120

<210> SEQ ID NO 8
<211> LENGTH: 109
<212> TYPE: PRT
<213> ORGANISM: Artificial
<220> FEATURE:
<223> OTHER INFORMATION: Bifunctional peptide TLT-3

<400> SEQUENCE: 8

Gly Pro Leu Gly Ser Thr Thr Trp Glu Ala Trp Asp Arg Ala Ile Ala
1               5                   10                  15

Glu Tyr Ala Ala Arg Ile Glu Ala Leu Leu Arg Ala Leu Gln Glu Gln
            20                  25                  30

Gln Glu Lys Asn Glu Ala Ala Leu Arg Glu Leu Gly Gly Gly Gly Ser
        35                  40                  45

Gly Gly Gly Gly Ser Gly Gly Gly Ser Gly Gly Gly Ser Gly
    50                  55                  60

Gly Gly Ser Gly Gly Gly Gly Ser Tyr Thr Ser Leu Ile His Ser
65                  70                  75                  80

Leu Ile Glu Glu Ser Gln Asn Gln Gln Glu Lys Asn Glu Gln Glu Leu
                85                  90                  95

Leu Glu Leu Asp Lys Trp Ala Ser Leu Trp Asn Trp Phe
            100                 105

<210> SEQ ID NO 9
<211> LENGTH: 8
<212> TYPE: PRT
<213> ORGANISM: Human immunodeficiency virus

<400> SEQUENCE: 9

Trp Met Glu Trp Asp Arg Glu Ile
1               5

<210> SEQ ID NO 10
<211> LENGTH: 30
<212> TYPE: PRT
<213> ORGANISM: Human immunodeficiency virus

<400> SEQUENCE: 10

Asn Asn Tyr Thr Ser Leu Ile His Ser Leu Ile Glu Glu Ser Gln Asn
1               5                   10                  15

Gln Gln Glu Lys Asn Glu Gln Glu Leu Leu Glu Leu Asp Lys
            20                  25                  30

<210> SEQ ID NO 11
<211> LENGTH: 34
<212> TYPE: PRT
<213> ORGANISM: Human immunodeficiency virus

<400> SEQUENCE: 11

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu

```
<210> SEQ ID NO 12
<211> LENGTH: 36
<212> TYPE: PRT
<213> ORGANISM: Human immunodeficiency virus

<400> SEQUENCE: 12

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu Glu Leu
        35

<210> SEQ ID NO 13
<211> LENGTH: 46
<212> TYPE: PRT
<213> ORGANISM: Human immunodeficiency virus

<400> SEQUENCE: 13

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu Glu Leu Asp Lys Trp Ala Ser Leu Trp Asn Trp Phe
        35                  40                  45

<210> SEQ ID NO 14
<211> LENGTH: 36
<212> TYPE: PRT
<213> ORGANISM: Human immunodeficiency virus

<400> SEQUENCE: 14

Ser Trp Glu Thr Trp Glu Arg Glu Ile Glu Asn Tyr Thr Lys Gln Ile
1               5                   10                  15

Tyr Lys Ile Leu Glu Glu Ser Gln Glu Gln Gln Asp Arg Asn Glu Lys
            20                  25                  30

Asp Leu Leu Glu
        35

<210> SEQ ID NO 15
<211> LENGTH: 35
<212> TYPE: PRT
<213> ORGANISM: Human immunodeficiency virus

<400> SEQUENCE: 15

Trp Glu Glu Trp Asp Lys Lys Ile Glu Glu Tyr Thr Lys Lys Ile Glu
1               5                   10                  15

Glu Leu Ile Lys Lys Ser Glu Glu Gln Gln Lys Lys Asn Glu Glu Glu
            20                  25                  30

Leu Lys Lys
        35

<210> SEQ ID NO 16
<211> LENGTH: 32
<212> TYPE: PRT
<213> ORGANISM: Human immunodeficiency virus

<400> SEQUENCE: 16

Gln Ile Trp Asn Asn Met Thr Trp Met Glu Trp Asp Arg Glu Ile Asn
1               5                   10                  15

Asn Tyr Thr Ser Leu Ile His Ser Leu Ile Glu Glu Ser Gln Asn Gln
```

-continued

```
<210> SEQ ID NO 17
<211> LENGTH: 30
<212> TYPE: PRT
<213> ORGANISM: Human immunodeficiency virus

<400> SEQUENCE: 17

Val Glu Asn Glu Thr Trp Met Glu Trp Glu Arg Glu Ile Glu Asn Tyr
1               5                   10                  15

Thr Lys Leu Ile Tyr Lys Ile Leu Glu Glu Ser Gln Glu Gln
            20                  25                  30

<210> SEQ ID NO 18
<211> LENGTH: 39
<212> TYPE: PRT
<213> ORGANISM: Human immunodeficiency virus

<400> SEQUENCE: 18

Trp Gln Glu Trp Glu Gln Lys Ile Thr Ala Leu Leu Glu Gln Ala Gln
1               5                   10                  15

Ile Gln Gln Glu Lys Asn Glu Tyr Glu Leu Gln Lys Leu Asp Lys Trp
            20                  25                  30

Ala Ser Leu Trp Glu Trp Phe
        35

<210> SEQ ID NO 19
<211> LENGTH: 36
<212> TYPE: PRT
<213> ORGANISM: Human immunodeficiency virus

<400> SEQUENCE: 19

Trp Met Glu Trp Asp Arg Glu Ile Glu Glu Tyr Thr Lys Lys Ile Glu
1               5                   10                  15

Glu Tyr Thr Lys Lys Ile Glu Glu Tyr Thr Lys Lys Ile Glu Glu Tyr
            20                  25                  30

Thr Lys Lys Ile
        35

<210> SEQ ID NO 20
<211> LENGTH: 36
<212> TYPE: PRT
<213> ORGANISM: Human immunodeficiency virus

<400> SEQUENCE: 20

Trp Asn His Thr Thr Trp Met Glu Trp Asp Arg Glu Ile Asn Asn Tyr
1               5                   10                  15

Thr Ser Leu Ile His Ser Leu Ile Glu Glu Ser Gln Asn Gln Gln Glu
            20                  25                  30

Lys Asn Glu Gln
        35

<210> SEQ ID NO 21
<211> LENGTH: 8
<212> TYPE: PRT
<213> ORGANISM: Human immunodeficiency virus

<400> SEQUENCE: 21

Trp Ala Ser Leu Trp Asn Trp Phe
1               5
```

```
<210> SEQ ID NO 22
<211> LENGTH: 36
<212> TYPE: PRT
<213> ORGANISM: Human immunodeficiency virus

<400> SEQUENCE: 22

His Ser Leu Ile Glu Glu Ser Gln Asn Gln Gln Glu Lys Asn Glu Gln
1               5                   10                  15

Glu Leu Leu Glu Leu Asp Lys Trp Ala Ser Leu Trp Asn Trp Phe Asn
            20                  25                  30

Ile Thr Asn Trp
            35

<210> SEQ ID NO 23
<211> LENGTH: 36
<212> TYPE: PRT
<213> ORGANISM: Human immunodeficiency virus

<400> SEQUENCE: 23

Glu Glu Tyr Thr Lys Lys Ile Glu Glu Tyr Thr Lys Lys Ile Glu Glu
1               5                   10                  15

Tyr Thr Lys Lys Ile Glu Glu Tyr Thr Lys Lys Ile Trp Ala Ser Leu
            20                  25                  30

Trp Asn Trp Phe
            35

<210> SEQ ID NO 24
<211> LENGTH: 114
<212> TYPE: PRT
<213> ORGANISM: Artificial
<220> FEATURE:
<223> OTHER INFORMATION: Bifunctional peptide TLT-4

<400> SEQUENCE: 24

Gly Pro Leu Gly Ser Thr Thr Trp Glu Ala Trp Asp Arg Ala Ile Ala
1               5                   10                  15

Glu Tyr Ala Ala Arg Ile Glu Ala Leu Leu Arg Ala Leu Gln Glu Gln
            20                  25                  30

Gln Glu Lys Asn Glu Ala Ala Leu Arg Glu Leu Gly Gly Gly Gly Ser
            35                  40                  45

Gly Gly Gly Gly Ser Gly Gly Gly Ser Gly Gly Gly Ser Gly
    50                  55                  60

Gly Gly Ser Gly Gly Gly Ser Gly Gly Gly Ser Tyr Thr
65                  70                  75              80

Ser Leu Ile His Ser Leu Ile Glu Glu Ser Gln Asn Gln Gln Glu Lys
                85                  90                  95

Asn Glu Gln Glu Leu Leu Glu Leu Asp Lys Trp Ala Ser Leu Trp Asn
            100                 105                 110

Trp Phe

<210> SEQ ID NO 25
<211> LENGTH: 109
<212> TYPE: PRT
<213> ORGANISM: Artificial
<220> FEATURE:
<223> OTHER INFORMATION: Bifunctional peptide TLT-5

<400> SEQUENCE: 25

Thr Thr Trp Glu Ala Trp Asp Arg Ala Ile Ala Glu Tyr Ala Ala Arg
1               5                   10                  15
```

```
Ile Glu Ala Leu Leu Arg Ala Leu Gln Glu Gln Gln Glu Lys Asn Glu
            20                  25                  30

Ala Ala Leu Arg Glu Leu Gly Gly Gly Gly Ser Gly Gly Gly Gly Ser
        35                  40                  45

Gly Gly Gly Gly Ser Gly Gly Gly Ser Gly Gly Gly Ser Gly
 50                  55                  60

Gly Gly Gly Ser Gly Gly Gly Ser Tyr Thr Ser Leu Ile His Ser
 65                  70                  75                  80

Leu Ile Glu Glu Ser Gln Asn Gln Gln Lys Asn Glu Gln Glu Leu
                85                  90                  95

Leu Glu Leu Asp Lys Trp Ala Ser Leu Trp Asn Trp Phe
            100                 105
```

<210> SEQ ID NO 26
<211> LENGTH: 104
<212> TYPE: PRT
<213> ORGANISM: Artificial
<220> FEATURE:
<223> OTHER INFORMATION: Bifunctional peptide TLT-6

<400> SEQUENCE: 26

```
Thr Thr Trp Glu Ala Trp Asp Arg Ala Ile Ala Glu Tyr Ala Ala Arg
1               5                   10                  15

Ile Glu Ala Leu Leu Arg Ala Leu Gln Glu Gln Gln Glu Lys Asn Glu
            20                  25                  30

Ala Ala Leu Arg Glu Leu Gly Gly Gly Gly Ser Gly Gly Gly Gly Ser
        35                  40                  45

Gly Gly Gly Gly Ser Gly Gly Gly Ser Gly Gly Gly Ser Gly
 50                  55                  60

Gly Gly Ser Tyr Thr Ser Leu Ile His Ser Leu Ile Glu Glu Ser
 65                  70                  75                  80

Gln Asn Gln Gln Glu Lys Asn Glu Gln Glu Leu Leu Glu Leu Asp Lys
                85                  90                  95

Trp Ala Ser Leu Trp Asn Trp Phe
            100
```

<210> SEQ ID NO 27
<211> LENGTH: 99
<212> TYPE: PRT
<213> ORGANISM: Artificial
<220> FEATURE:
<223> OTHER INFORMATION: Bifunctional peptide TLT-7

<400> SEQUENCE: 27

```
Thr Thr Trp Glu Ala Trp Asp Arg Ala Ile Ala Glu Tyr Ala Ala Arg
1               5                   10                  15

Ile Glu Ala Leu Leu Arg Ala Leu Gln Glu Gln Gln Glu Lys Asn Glu
            20                  25                  30

Ala Ala Leu Arg Glu Leu Gly Gly Gly Gly Ser Gly Gly Gly Gly Ser
        35                  40                  45

Gly Gly Gly Gly Ser Gly Gly Gly Ser Gly Gly Gly Ser Tyr
 50                  55                  60

Thr Ser Leu Ile His Ser Leu Ile Glu Glu Ser Gln Asn Gln Gln Glu
 65                  70                  75                  80

Lys Asn Glu Gln Glu Leu Leu Glu Leu Asp Lys Trp Ala Ser Leu Trp
                85                  90                  95

Asn Trp Phe
```

```
<210> SEQ ID NO 28
<211> LENGTH: 94
<212> TYPE: PRT
<213> ORGANISM: Artificial
<220> FEATURE:
<223> OTHER INFORMATION: Bifunctional peptide TLT-8

<400> SEQUENCE: 28

Thr Thr Trp Glu Ala Trp Asp Arg Ala Ile Ala Glu Tyr Ala Ala Arg
1               5                   10                  15

Ile Glu Ala Leu Leu Arg Ala Leu Gln Glu Gln Gln Glu Lys Asn Glu
            20                  25                  30

Ala Ala Leu Arg Glu Leu Gly Gly Gly Ser Gly Gly Gly Gly Gly Ser
        35                  40                  45

Gly Gly Gly Gly Ser Gly Gly Gly Ser Tyr Thr Ser Leu Ile His
    50                  55                  60

Ser Leu Ile Glu Glu Ser Gln Asn Gln Gln Glu Lys Asn Glu Gln Glu
65                  70                  75                  80

Leu Leu Glu Leu Asp Lys Trp Ala Ser Leu Trp Asn Trp Phe
                85                  90

<210> SEQ ID NO 29
<211> LENGTH: 105
<212> TYPE: PRT
<213> ORGANISM: Artificial
<220> FEATURE:
<223> OTHER INFORMATION: Bifunctional peptide TLT-9

<400> SEQUENCE: 29

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu Gly Gly Gly Gly Ser Gly Gly Gly Gly Ser Gly Gly Gly Gly
        35                  40                  45

Ser Gly Gly Gly Gly Ser Gly Gly Gly Gly Ser Gly Gly Gly Gly Ser
    50                  55                  60

Gly Gly Gly Gly Ser Tyr Thr Ser Leu Ile His Ser Leu Ile Glu Glu
65                  70                  75                  80

Ser Gln Asn Gln Gln Glu Lys Asn Glu Gln Glu Leu Leu Glu Leu Asp
                85                  90                  95

Lys Trp Ala Ser Leu Trp Asn Trp Phe
            100                 105

<210> SEQ ID NO 30
<211> LENGTH: 107
<212> TYPE: PRT
<213> ORGANISM: Artificial
<220> FEATURE:
<223> OTHER INFORMATION: Bifunctional peptide TLT-10

<400> SEQUENCE: 30

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu Glu Leu Gly Gly Gly Gly Ser Gly Gly Gly Gly Ser Gly Gly
        35                  40                  45

Gly Gly Ser Gly Gly Gly Gly Ser Gly Gly Gly Gly Ser Gly Gly Gly
```

```
                    50                  55                  60
Gly Ser Gly Gly Gly Ser Tyr Thr Ser Leu Ile His Ser Leu Ile
 65                  70                  75                  80

Glu Glu Ser Gln Asn Gln Gln Glu Lys Asn Glu Gln Glu Leu Leu Glu
                 85                  90                  95

Leu Asp Lys Trp Ala Ser Leu Trp Asn Trp Phe
                100                 105
```

<210> SEQ ID NO 31
<211> LENGTH: 109
<212> TYPE: PRT
<213> ORGANISM: Artificial
<220> FEATURE:
<223> OTHER INFORMATION: Bifunctional peptide TLT-11

<400> SEQUENCE: 31

```
Thr Thr Trp Met Glu Trp Asp Arg Glu Ile Asn Asn Tyr Thr Ser Leu
 1               5                  10                  15

Ile His Ser Leu Ile Glu Glu Ser Gln Asn Gln Gln Glu Lys Asn Glu
                20                  25                  30

Gln Glu Leu Leu Glu Leu Gly Gly Gly Gly Ser Gly Gly Gly Gly Ser
                35                  40                  45

Gly Gly Gly Gly Ser Gly Gly Gly Ser Gly Gly Gly Ser Gly
         50                  55                  60

Gly Gly Ser Gly Gly Gly Gly Ser Tyr Thr Ser Leu Ile His Ser
 65                  70                  75                  80

Leu Ile Glu Glu Ser Gln Asn Gln Gln Glu Lys Asn Gln Glu Leu
                85                  90                  95

Leu Glu Leu Asp Lys Trp Ala Ser Leu Trp Asn Trp Phe
                100                 105
```

<210> SEQ ID NO 32
<211> LENGTH: 109
<212> TYPE: PRT
<213> ORGANISM: Artificial
<220> FEATURE:
<223> OTHER INFORMATION: Bifunctional peptide TLT-12

<400> SEQUENCE: 32

```
Thr Thr Trp Met Glu Trp Asp Arg Glu Ile Asn Asn Tyr Thr Ser Leu
 1               5                  10                  15

Ile His Ser Leu Ile Glu Glu Ser Gln Asn Gln Gln Glu Lys Asn Glu
                20                  25                  30

Gln Glu Leu Leu Glu Leu Gly Gly Gly Gly Ser Gly Gly Gly Ser
                35                  40                  45

Gly Gly Gly Gly Ser Gly Gly Gly Ser Gly Gly Gly Ser Gly
         50                  55                  60

Gly Gly Ser Gly Gly Gly Ser His Ser Leu Ile Glu Glu Ser
 65                  70                  75                  80

Gln Asn Gln Gln Glu Lys Asn Glu Gln Glu Leu Leu Glu Leu Asp Lys
                85                  90                  95

Trp Ala Ser Leu Trp Asn Trp Phe Asn Ile Thr Asn Trp
                100                 105
```

<210> SEQ ID NO 33
<211> LENGTH: 109
<212> TYPE: PRT
<213> ORGANISM: Artificial
<220> FEATURE:

<223> OTHER INFORMATION: Bifunctional peptide TLT-13

<400> SEQUENCE: 33

Thr Thr Trp Met Glu Trp Asp Arg Glu Ile Asn Asn Tyr Thr Ser Leu
1               5                   10                  15

Ile His Ser Leu Ile Glu Glu Ser Gln Asn Gln Gln Glu Lys Asn Glu
                20                  25                  30

Gln Glu Leu Leu Glu Leu Gly Gly Gly Gly Ser Gly Gly Gly Gly Ser
            35                  40                  45

Gly Gly Gly Gly Ser Gly Gly Gly Ser Gly Gly Gly Gly Ser Gly
        50                  55                  60

Gly Gly Gly Ser Gly Gly Gly Ser Glu Glu Tyr Thr Lys Lys Ile
65                  70                  75                  80

Glu Glu Tyr Thr Lys Lys Ile Glu Glu Tyr Thr Lys Lys Ile Glu Glu
                85                  90                  95

Tyr Thr Lys Lys Ile Trp Ala Ser Leu Trp Asn Trp Phe
            100                 105

<210> SEQ ID NO 34
<211> LENGTH: 109
<212> TYPE: PRT
<213> ORGANISM: Artificial
<220> FEATURE:
<223> OTHER INFORMATION: Bifunctional peptide TLT-14

<400> SEQUENCE: 34

Thr Thr Trp Met Glu Trp Asp Arg Glu Ile Asn Asn Tyr Thr Ser Leu
1               5                   10                  15

Ile His Ser Leu Ile Glu Glu Ser Gln Asn Gln Gln Glu Lys Asn Glu
                20                  25                  30

Gln Glu Leu Leu Glu Leu Gly Gly Gly Gly Ser Gly Gly Gly Gly Ser
            35                  40                  45

Gly Gly Gly Gly Ser Gly Gly Gly Ser Gly Gly Gly Gly Ser Gly
        50                  55                  60

Gly Gly Gly Ser Gly Gly Gly Ser Glu Glu Leu Ala Lys Lys Ala
65                  70                  75                  80

Glu Glu Leu Ala Lys Lys Ala Glu Glu Leu Ala Lys Lys Ala Glu Glu
                85                  90                  95

Leu Ala Lys Lys Ala Trp Ala Ser Leu Trp Asn Trp Phe
            100                 105

<210> SEQ ID NO 35
<211> LENGTH: 10
<212> TYPE: PRT
<213> ORGANISM: Artificial
<220> FEATURE:
<223> OTHER INFORMATION: L10 linker

<400> SEQUENCE: 35

Gly Gly Gly Gly Ser Gly Gly Gly Gly Ser
1               5                   10

<210> SEQ ID NO 36
<211> LENGTH: 15
<212> TYPE: PRT
<213> ORGANISM: Artificial
<220> FEATURE:
<223> OTHER INFORMATION: L15 linker

<400> SEQUENCE: 36

```
Gly Gly Gly Gly Ser Gly Gly Gly Gly Ser Gly Gly Gly Ser
1               5                   10                  15
```

<210> SEQ ID NO 37
<211> LENGTH: 20
<212> TYPE: PRT
<213> ORGANISM: Artificial
<220> FEATURE:
<223> OTHER INFORMATION: L20 linker

<400> SEQUENCE: 37

```
Gly Gly Gly Gly Ser Gly Gly Gly Gly Ser Gly Gly Gly Gly Ser Gly
1               5                   10                  15

Gly Gly Gly Ser
            20
```

<210> SEQ ID NO 38
<211> LENGTH: 25
<212> TYPE: PRT
<213> ORGANISM: Artificial
<220> FEATURE:
<223> OTHER INFORMATION: L25 linker

<400> SEQUENCE: 38

```
Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25
```

<210> SEQ ID NO 39
<211> LENGTH: 30
<212> TYPE: PRT
<213> ORGANISM: Artificial
<220> FEATURE:
<223> OTHER INFORMATION: L30 linker

<400> SEQUENCE: 39

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30
```

<210> SEQ ID NO 40
<211> LENGTH: 35
<212> TYPE: PRT
<213> ORGANISM: Artificial
<220> FEATURE:
<223> OTHER INFORMATION: L35 linker

<400> SEQUENCE: 40

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35
```

<210> SEQ ID NO 41
<211> LENGTH: 40
<212> TYPE: PRT
<213> ORGANISM: Artificial
<220> FEATURE:
<223> OTHER INFORMATION: L40 linker

<400> SEQUENCE: 41

```
Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
            20                  25                  30

Gly Gly Ser Gly Gly Gly Ser
        35              40

<210> SEQ ID NO 42
<211> LENGTH: 9
<212> TYPE: PRT
<213> ORGANISM: Artificial
<220> FEATURE:
<223> OTHER INFORMATION: C-terminal extension sequence

<400> SEQUENCE: 42

Asn Ser Ser Gly Arg Ile Val Thr Asp
1               5

<210> SEQ ID NO 43
<211> LENGTH: 34
<212> TYPE: PRT
<213> ORGANISM: Human immunodeficiency virus

<400> SEQUENCE: 43

Ser Gly Ile Val Gln Gln Gln Asn Asn Leu Leu Arg Ala Ile Glu Ala
1               5                   10                  15

Gln Gln His Leu Leu Gln Leu Thr Val Trp Gly Ile Lys Gln Leu Gln
                20                  25                  30

Ala Arg

<210> SEQ ID NO 44
<211> LENGTH: 36
<212> TYPE: PRT
<213> ORGANISM: Human immunodeficiency virus

<400> SEQUENCE: 44

Ser Gly Ile Val Gln Gln Gln Asn Asn Leu Leu Arg Ala Ile Glu Ala
1               5                   10                  15

Gln Gln His Leu Leu Gln Leu Thr Val Trp Gly Ile Lys Gln Leu Gln
                20                  25                  30

Ala Arg Ile Leu
        35

<210> SEQ ID NO 45
<211> LENGTH: 51
<212> TYPE: PRT
<213> ORGANISM: Human immunodeficiency virus

<400> SEQUENCE: 45

Gln Ala Arg Gln Leu Leu Ser Gly Ile Val Gln Gln Gln Asn Asn Leu
1               5                   10                  15

Leu Arg Ala Ile Glu Ala Gln Gln His Leu Leu Gln Leu Thr Val Trp
                20                  25                  30

Gly Ile Lys Gln Leu Gln Ala Arg Ile Leu Ala Val Glu Arg Tyr Leu
            35                  40                  45

Lys Gln Gln
    50

<210> SEQ ID NO 46
<211> LENGTH: 38
```

<212> TYPE: PRT
<213> ORGANISM: Human immunodeficiency virus

<400> SEQUENCE: 46

Asn Asn Leu Leu Arg Ala Ile Glu Ala Gln Gln His Leu Leu Gln Leu
1               5                   10                  15

Thr Val Trp Gly Ile Lys Gln Leu Gln Ala Arg Ile Leu Ala Val Glu
            20                  25                  30

Arg Tyr Leu Lys Asp Gln
        35

<210> SEQ ID NO 47
<211> LENGTH: 82
<212> TYPE: DNA
<213> ORGANISM: Artificial
<220> FEATURE:
<223> OTHER INFORMATION: FT1144 primer

<400> SEQUENCE: 47
ccggggatcc acgacctggg aagcatggga cagagctatt gctgaatacg cagctaggat    60
agaagcttta ctcagagctt ta                                              82

<210> SEQ ID NO 48
<211> LENGTH: 75
<212> TYPE: DNA
<213> ORGANISM: Artificial
<220> FEATURE:
<223> OTHER INFORMATION: RT1144 primer

<400> SEQUENCE: 48
acttcctcct cctcctaatt cccttaaggc tgcttcattc ttttcttgct gttcttgtaa    60
agctctgagt aaagc                                                      75

<210> SEQ ID NO 49
<211> LENGTH: 81
<212> TYPE: DNA
<213> ORGANISM: Artificial
<220> FEATURE:
<223> OTHER INFORMATION: FL35 primer

<400> SEQUENCE: 49
ggaggaggag gaagtggcgg cggcggctcg ggtggtggtg gttctggagg tggcggtagc    60
ggaggtggag gtagtggagg c                                               81

<210> SEQ ID NO 50
<211> LENGTH: 79
<212> TYPE: DNA
<213> ORGANISM: Artificial
<220> FEATURE:
<223> OTHER INFORMATION: RL35 primer

<400> SEQUENCE: 50
gctacctccg cctcccgaac ctccgcctcc actacctcca cctccgctac cgccacctcc    60
agaaccacca ccacccgag                                                  79

<210> SEQ ID NO 51
<211> LENGTH: 78
<212> TYPE: DNA
<213> ORGANISM: Artificial
<220> FEATURE:
<223> OTHER INFORMATION: FT20 primer

<400> SEQUENCE: 51

```
ggaggcggag gtagctacac aagcttaata cactccttaa ttgaagaatc gcaaaaccag    60
caagaaaaga atgaacaa                                                  78

<210> SEQ ID NO 52
<211> LENGTH: 72
<212> TYPE: DNA
<213> ORGANISM: Artificial
<220> FEATURE:
<223> OTHER INFORMATION: RT20 primer

<400> SEQUENCE: 52
ccgctcgagt taaaccaat tccacaaact tgcccattta tctaattcca ataattcttg    60
ttcattcttt tc                                                        72

<210> SEQ ID NO 53
<211> LENGTH: 9
<212> TYPE: PRT
<213> ORGANISM: Artificial
<220> FEATURE:
<223> OTHER INFORMATION: C-terminal extension sequence

<400> SEQUENCE: 53

Tyr Ser Ser Gly Arg Ile Val Thr Asp
1               5
```

BIFUNCTIONAL MOLECULES FOR INHIBITING HIV ENTRY

CROSS REFERENCE TO RELATED APPLICATIONS

The present application claims the benefit under 35 USC §119(e) to U.S. Provisional Patent Application 61/056,580 filed May 28, 2008, the entire contents of which are incorporated by reference herein.

FIELD OF THE INVENTION

The present disclosure relates to the field of anti-viral agents. Specifically, the present disclosure relates to anti-viral agents comprising bifunctional molecules which inhibit entry of the human immunodeficiency virus into target cells.

BACKGROUND OF THE INVENTION

By the end of 2007, about 33.2 million people in the world were living infected with the human immunodeficiency virus (HIV) and more than 25 million people have died of acquired immunodeficiency syndrome (AIDS). Therefore, it is urgently needed to discover and develop new therapeutic strategies against HIV infection. So far, 28 anti-HIV drugs have been approved by the United States Food and Drug Administration to treat people infected with HIV, including 15 reverse transcriptase inhibitors (RTIs), 10 protease inhibitors (PIs), one integrase inhibitor (II), and two entry inhibitors (EIs). All the RTIs, PIs, and II inhibit HIV replication after the virus gets into the host cells, while the two EIs can block HIV entry into the host cell.

HIV entry is initiated by binding of the envelope glycoprotein (Env) surface subunit gp120 to the primary receptor CD4 and then to a chemokine receptor (CCR5 or CXCR4) on the target cell. These interactions trigger gp41 structural rearrangement, resulting in the formation of a stable gp41 six-helix bundle (6-HB) core structure, which brings the both the viral and target cell membranes into proximity for fusion. In the 6-HB, three N-terminal heptad repeats (NHR or HR1) associate to form the central trimeric coiled coil, while three C-terminal heptad repeat (CHR or HR2) pack obliquely in an anti-parallel manner into the highly conserved hydrophobic grooves on the surface of the NHR-trimer. In each groove, there is a highly conserved hydrophobic deep pocket formed by the pocket-forming sequence (residues 565-581) in the NHR region. This pocket plays a critical role in viral fusion and maintaining the stability of the 6-HB.

One of the FDA-approved EIs is a synthetic peptide designed based on the HIV-1 gp41 CHR sequence (aa 638-673), named T20 (generic name: enfuvirtide, brand name: Fuzeon® [Trimeris]). T20 contains an HR (heptad repeat)-binding domain (HBD) and a tryptophan-rich domain (TRD) (FIG. 1), through which T20 can bind to the HR-sequence, especially the GIV motif in NHR, and the target cell membrane, respectively, to inhibit HIV fusion with and entry into the target cell.

The clinical of application of T20 is limited because of the rapid emergence of T20-resistant viruses in T20-treated patients. Both in vitro and in vivo studies have shown that T20 resistance is associated with single or double mutations in the GIV and the adjacent region (aa 36-45) in the gp41 NHR domain (e.g., G36D, I37V, V38A, V38E, V38M, N42D, N42S, and N43D) because this region is the primary binding site in gp41 and these mutations impact the binding of T20 to the viral gp41 NHR region. Since the binding of T20 to the HR sequence in the NHR domain is not strong enough to compete with the interaction between the viral gp41 CHR and NHR regions, T20 has to use its C-terminal TRD to interact with the target cell membrane in order to stabilize its interaction with the viral gp41 NHR region. Another weakness of the T20 peptide as an anti-HIV drug is that it has to be administrated by injection twice daily at high dosage (90 mg/dose), resulting in painful injection-site reactions in most patients. Furthermore, because of the high production cost of peptide synthesis, T20 is exorbitantly expensive for use, especially in developing countries.

C38 is a 38-mer peptide derived from aa 626-673 of the HIV-1 gp41 CHR region. It contains a pocket-binding domain (PBD) and an HBD (FIG. 1), through which C38 binds to the pocket-forming sequence and the HR-sequence in the viral gp41 NHR region to form stable heterologous 6-HB and block the fusion-active gp41 core formation. This results in inhibition of HIV fusion with, and entry into, the host cell. Because the primary binding site of C38 is the pocket-forming sequence, rather than the aa 36-45 region, the mutations in the GIV motif and the adjacent region in the gp41 NHR domain T1144 do not significantly affect the binding of C38. Therefore, the viruses with mutations in the aa 36-45 are resistant to T20, but sensitive to C38.

T1144 is also a 38-mer peptide containing a PBD and an HBD (FIG. 1). It was designed by modifying the amino acid sequence of C38 to increase α-helicity and 6-HB stability and to improve pharmacokinetic properties. Like C38, T1144 is much more effective than T20 against both the R5 and X4 strains of HIV-1, including those resistant to T20.

One recent study has shown that the combination of a CHR peptide containing the PBDn (e.g., C34, C38, T1144) and a CHR peptide lacking the PBD (e.g., T20) exhibits potent synergistic effect against both T20-sensitive and resistant viruses.

BRIEF DESCRIPTION OF THE DRAWINGS

FIG. 6A—Inhibition of infection by primary HIV-1 isolate 93IN101 (subtype C, R5) in PBMCs as determined by p24 assay.

FIG. 10 depicts the secondary structure of TLT-1, as determined by circular dichroism (CD), and its ability to form 6-HB with NHR peptides.

SUMMARY OF THE INVENTION

Figure 1:
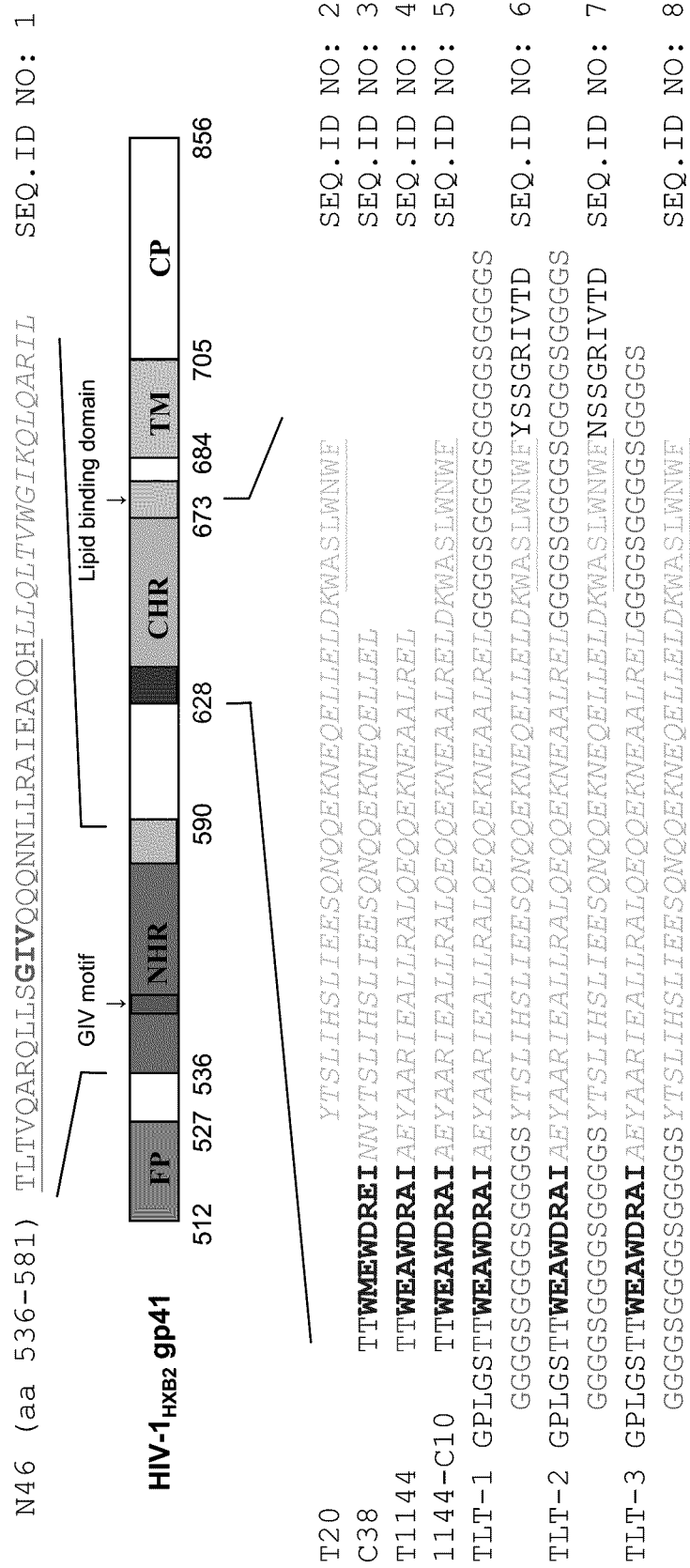
FIG. 1 depicts bifunctional HIV entry inhibitor design, a schematic view of the HIV-1$_{HXB2}$ gp41 molecule and sequences of exemplary HIV entry inhibitors. FP, fusion peptide; NHR, N-terminal heptad repeat; CHR, C-terminal heptad repeat; TR, tryptophan-rich domain; TM, transmembrane domain; CP, cytoplasmic domain. PBD (pocket-binding domain), HBD (heptad repeat-binding domain), and TRD (tryptophan-rich domain) in the CHR peptides are highlighted in bold, italic and underline, respectively. The heptad repeat (HR) sequence, the GIV motif (determinant for T20 resistance) and the pocket-forming sequence in the NHR are highlighted in underline, bold and italic, respectively.
Figure 2:
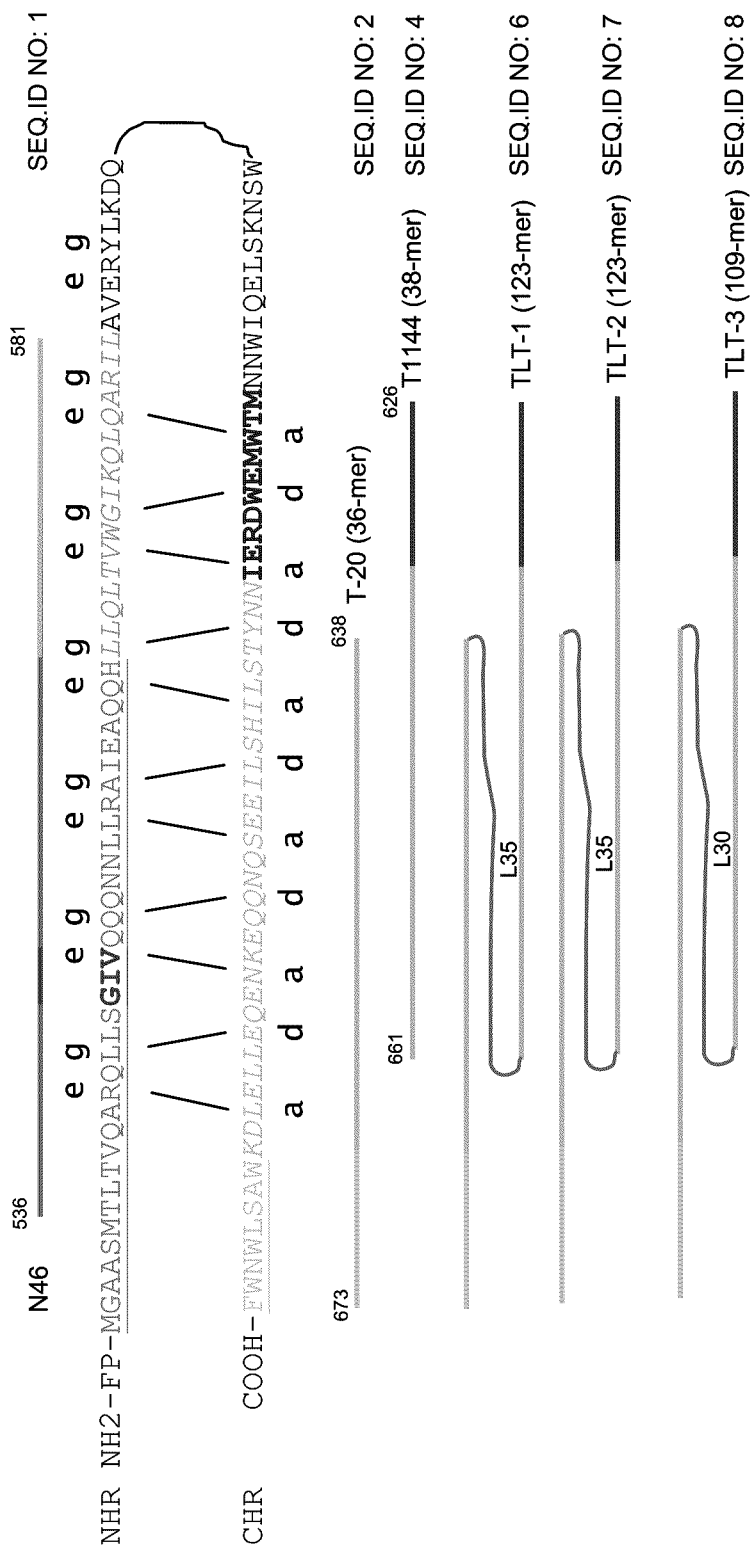
FIG. 2 depicts the interaction between the NHR and CHR peptides. The lines between the NHR and CHR domains indicate the interaction between the residues located at the e, g and the a, d positions in the NHR and CHR, respectively. The interaction between the PBD and pocket-forming sequence is critical for stabilization of the 6-helical bundle (6-HB).

Bifunctional molecules which inhibit HIV entry into the target cell are disclosed herein. These molecules can be used as a therapeutic agent for treatment of patents infected by HIV, including non-B and multi-drug resistant strains, through a mechanism of action that is different from current anti-HIV drugs.

Bifunctional molecules were designed and expressed in *E. coli* as recombinant HIV entry inhibitors for treating and preventing infection by HIV-1 strains, including those resistant to T20 and other antiretroviral drugs. Each of the bifunctional molecule contains a CHR peptide containing the pocket-binding domain and HR-binding domain, a linker, and a CHR peptide consisting of the HR-binding sequence and a tryptophan-rich domain. Compared with the synthetic CHR peptides, the TLT-1-based bifunctional molecules have the following advantages: i) they have more potent anti-HIV activity; ii) they are more effective against T20-resistant viruses; iii) they can be expressed in *E. coli* expression systems in large quantity, thus having much lower production cost; iv) they are less sensitive to the proteolytic enzymes; v) they are more stable in biological solutions; and vi) they bind more strongly to the NHR peptide to form highly stable 6-HB.

In one embodiment, disclosed herein is a bifunctional molecule comprising a first C-terminal heptad repeat (CHR) peptide containing a pocket-binding domain and a heptad repeat (HR)-binding domain linked to a flexible linker, which in turn is linked to a second CHR peptide containing a HR-binding domain and a tryptophan-rich domain.

In another embodiment, the first CHR peptide comprises the amino acid sequence selected from the group consisting of C34 (SEQ ID NO:11), C36 (SEQ ID NO:12), C38 (SEQ ID NO:3), C46 (SEQ ID NO:13), T1144 (SEQ ID NO:4), T1144-C10 (SEQ ID NO:5), sifuvirtide (SEQ ID NO:14), C35-EK (SEQ ID NO:15), CP621-652 (SEQ ID NO:16), CP32M (SEQ ID NO:17), T1249 (SEQ ID NO:18), PBD-4HR (SEQ ID NO:19), and C36B (SEQ ID NO:20).

In another embodiment, the second CHR peptide comprises the amino acid sequence selected from the group consisting of T20 (SEQ ID NO:2), T20-A (SEQ ID NO:22), and 4HR-LBD (SEQ ID NO:23).

In another embodiment, the flexible linker comprises the amino acid sequence (GGGGS)$_n$ (SEQ ID NOs: 35-41), wherein n is an integer between 2 and 8.

In yet another embodiment, the bifunctional molecule further comprises the amino acid sequence YSSGRIVTD (SEQ ID NO:53) or NSSGRIVTD (SEQ ID NO:42) at the C-terminus of the bifunctional molecule In yet another embodiment, the bifunctional molecule comprises the amino acid sequence of GPLGSTTWEAWD-RAIAEYAARIEALLRALQEQQEKNEAALREL (GGGGS)$_7$YTSLIHSLIEESQNQQEKNEQELLELDK-WASLWNWFYSSGRIVTD (SEQ ID NO: 6).

In yet another embodiment, the bifunctional molecule comprises the amino acid sequence of GPLGSTTWEAWD-RAIAEYAARIEALLRALQEQQEKNEAALREL (GGGGS)$_7$YTSLIHSLIEESQNQQEKNEQELLELDK-WASLWNWFNSSGRIVTD (SEQ ID NO: 7).

In yet another embodiment, the bifunctional molecule comprises the amino acid sequence of GPLGSTTWEAWD-RAIAEYAARIEALLRALQEQQEKNEAALREL (GGGGS)$_6$YTSLIHSLIEESQNQQEKNEQELLELDK-WASLWNWF (SEQ ID NO: 8).

In another embodiment, the bifunctional molecule is produced by recombinant DNA technology in an expression system selected from the group consisting of bacteria, yeast, insect cells and mammalian cells. In one embodiment, the bifunctional molecule is produced in *Escherichia coli*.

In another embodiment, the bifunctional molecule is synthesized on a solid or in solution. In yet another embodiment, the bifunctional molecule is synthesized as several separated segments and then connected together.

Also provided herein are methods of treating a human immunodeficiency virus infection comprising administering a bifunctional molecule as disclosed herein to an individual infected with the human immunodeficiency virus; inhibiting entry of the virus into a target cell, and blocking infection of the target cell with the virus.

Also provided herein are methods of preventing infection with a human immunodeficiency virus comprising administering a bifunctional molecule as disclosed herein to an individual at risk for infection with the human immunodeficiency virus; inhibiting entry of the virus into a target cell, and blocking infection of the target cell with the virus.

In another embodiment, pharmaceutical compositions are provided which comprise a bifunctional molecule comprising a first C-terminal heptad repeat (CHR) peptide containing a pocket-binding domain and a heptad repeat (HR)-binding domain linked to a flexible linker, which in turn is linked to a second CHR peptide containing a HR-binding domain and a tryptophan-rich domain. In another embodiment, the pharmaceutical composition comprises at least one pharmaceutically acceptable excipient in addition to the bifunctional molecule.

In yet another embodiment, the pharmaceutical compositions comprise more than one bifunctional molecule as disclosed herein. In another embodiment, the pharmaceutical compositions further comprises at least one additional antiviral agent.

DETAILED DESCRIPTION OF THE INVENTION

Bifunctional (chimeric) molecules are presented herein which consist of: (i) a C-terminal heptad repeat (CHR) peptide containing a pocket-binding domain (PBD) and a heptad repeat (HR)-binding domain (HBD), which binds to the pocket-forming sequence and HR sequence in the viral gp41 NHR region, respectively; (ii) a CHR peptide containing an HBD and a tryptophan-rich domain (TRD), which binds to the HR sequence in the viral gp41 NHR region and the lipid membrane of the target cell, respectively; and (iii) a flexible linker consisting of 10 to 40 amino acids linking the two CHR peptides so that these two functional domains can move freely to bind corresponding target proteins on human immunodeficiency virus (HIV) or HIV-infected cells. The bifunctional molecules are expressed in *E. coli*, yeast, insect cells or mammalian cells, purified by chromatography and tested for their inhibitory activity on HIV-mediated cell-cell fusion and HIV replication.

TABLE 1

Amino acid sequences of HIV regions

| Molecule | SEQ ID NO | Sequence |
|---|---|---|
| PBD | 9 | WMEWDREI |
| HBD | 10 | NNYTSLIHSLIEESQNQQEKNEQELLELDK |
| TRD | 21 | WASLWNWF |
| N34 | 43 | SGIVQQQNNLLRAIEAQQHLLQLTVWGIKQLQAR |
| N36 | 44 | SGIVQQQNNLLRAIEAQQHLLQLTVWGIKQLQARIL |
| N46 | 1 | TLTVQARQLLSGIVQQQNNLLRAIEAQQHLLQLTVWGIKQLQARIL |
| N51 | 45 | QARQLLSGIVQQQNNLLRAIEAQQHLLQLTVWGIKQLQARILAVERYLKQQ |
| DP-107 | 46 | NNLLRAIEAQQHLLQLTVWGIKQLQARILAVERYLKDQ |

Various bifunctional proteins were design by linking two CHR peptides containing different functional domains. The bifunctional entry inhibitors contain more than 100 amino acid residues and are therefore suitable for production as recombinant proteins and thus avoid the high cost of peptide synthesis.

An exemplary bifunctional HIV entry inhibitor TLT-1 (SEQ ID NO: 6) is composed of two CHR peptides, T1144 (SEQ ID NO: 4) and T20 (SEQ ID NO: 2). Both target gp41 NHR while having distinct and complementally functional domains: T1144 contains a PBD and a HBD, through which T1144 binds to the pocket-forming sequence and HR sequence in the viral gp41 NHR region, respectively, while T20 contains a HBD and a TRD, through which T20 interacts with the HR sequence in the viral gp41 NHR region and the lipid membrane of the target cells, respectively. In this way, TLT-1 simultaneously interacts with the gp41 NHR groove, deep pocket, and lipid membrane to prevent fusion core formation.

Figure 14:
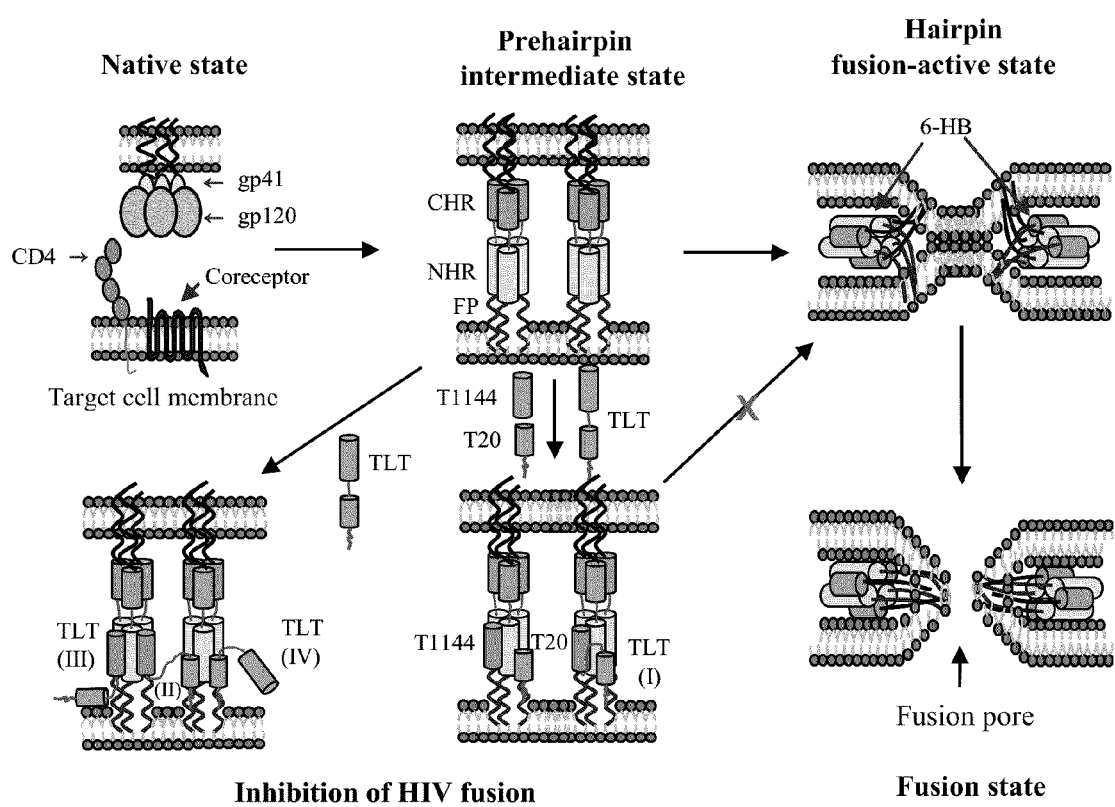
FIG. 14 depicts putative interaction models of HIV entry inhibitors. T20 and T1144 components contain distinct and complementary functional domains. T1144 binds to the HR sequence and pocket-forming sequence in the NHR domain via its HBD and PBD, respectively, to form stable heterologous 6-HB. T20 interacts with the HR sequence in NHR and lipid membranes or fusion lipid through its HBD and TRD, respectively. TLT bifunctional HIV entry inhibitors have four possible interaction models with gp41 NHR and lipid membrane, including but not limited to: TLT may interact with one NHR-trimer by occupying two grooves on the trimer with both T20 and T1144 components (Model I); TLT may interact with two NHR-trimers by occupying one groove on each trimer with both T20 and T1144 components (Model II); TLT may interact with one NHR-trimer by occupying one groove with either T1144 component (Model 111) or T20 component (Model IV).

The 35mer linker provides space for TLT-1 interaction with the NHR and lipid membrane through at least one of the multiple models depicted in FIG. 14. These models include, but are not limited to (i) interaction with one NHR-trimer by occupying two grooves on the trimer with both T20 and T1144 components (Model I); (ii) interaction with two NHR-trimers by occupying one groove on each trimer with both T20 and T1144 components; (iii) interaction with one NHR-trimer by occupying one groove with either the T1144 component (Model III) or the T20 component (Model IV). The two components of TLT-1 may not functional equally. For example, T1144 binds much stronger than T20 to NHR. Therefore, one of these interaction models may dominate others.

TLT-1 was successful expressed in *E. coli* with good yields and folded into a stable structure with high α-helical content. TLT-1 binds tightly with the N46 peptide and forms a highly thermal stable complex. Accordingly, TLT-1 strongly inhibits 6-HB formation and is highly active against HIV-1 gp41 mediated cell-cell fusion.

TLT-1 also demonstrated low nM activity against infection by various HIV-1 stains, especially the T20-resistant HIV-1 strains.

TLT-1 is stable in human sera and in the presence of peripheral blood mononuclear cells (PBMC) and is more resistant to proteolysis than either T20 or T1144 alone. The high stability suggests longer half-life and therefore this bifunctional molecule is predicted to be useful at lower dosages and with less administration frequency. The production of a recombinant protein is easier to scale-up than that of a synthetic peptide, suggesting the production cost for TLT-1 may be much lower than T20 and T1144. Low nM activity against various HIV-1 strains including T20 resistant strains suggests TLT-1 is suitable for clinical trail for patients fail to T20 treatment. Administration of TLT-1 may also delay the emergency of drug-resistant strains. The high antiretroviral profile suggests that the TLT-1 is promising to develop into new generation of HIV entry inhibitor.

TABLE 2

Components of the bifunctional HIV entry inhibitors

| Molecule | SEQ ID NO | Sequence |
|---|---|---|
| CHR peptides containing PBD and HBD | | |
| C34 | 11 | WMEWDREINNYTSLIHSLIEESQNQQEKNEQELL |
| C36 | 12 | WMEWDREINNYTSLIHSLIEESQNQQEKNEQELLEL |
| C38 | 3 | TTWMEWDREINNYTSLIHSLIEESQNQQEKNEQELLEL |
| C46 | 13 | WMEWDREINNYTSLIHSLIEESQNQQEKNEQELLELDKWASLWNWF |
| T1144 | 4 | TTWEAWDRAIAEYAARIEALLRALQEQQEKNEAALREL |
| T1144-C10 | 5 | TTWMAWDREINNYTSLIHSLIRRSQNQQEKNEQELLELDKWASLLWNWF |

TABLE 2-continued

Components of the bifunctional HIV entry inhibitors

| Molecule | SEQ ID NO | Sequence |
|---|---|---|
| Sifuvirtide | 14 | SWETWEREIENYTKQIYKILEESQEQQDRNEKDLLE |
| C35-EK | 15 | WEEWDKKIEEYTKKIEELIKKSEEQQKKNEEELKK |
| CP621-652 | 16 | QIWNNMTWMEWDREINNYTSLIHSLIEESQNQ |
| CP32M | 17 | VENETWMEWEREIENYTKLIYKILEESQEQ |
| T1249 | 18 | WQEWEQKITALLEQAQIQQEKNEYELQKLDKWASLWEWF |
| PBD-4HR | 19 | WMEWDREIEEYTKKIEEYTKKIEEYTKKIEEYTKKI |
| C36B | 20 | WNHTTWMEWDREINNYTSLIHSLIEESQNQQEKNEQ |
| CHR peptides containing TRD and HBD | | |
| T20 | 2 | YTSLIHSLIEESQNQQEKNEQELLELDKWASLWNWF |
| T20-A | 22 | HSLIEESQNQQEKNEQELLELDKWASLWNWFNITNW |
| 4HR-LBD | 23 | EEYTKKIEEYTKKIEEYTKKIEEYTKKIWASLWNWF |
| Flexible linkers | | |
| L10 | 35 | (GGGGS)$_2$ |
| L15 | 36 | (GGGGS)$_3$ |
| L20 | 37 | (GGGGS)$_4$ |
| L25 | 38 | (GGGGS)$_5$ |
| L30 | 39 | (GGGGS)$_6$ |
| L35 | 40 | (GGGGS)$_7$ |
| L40 | 41 | (GGGGS)$_8$ |

TABLE 3

Exemplary bifunctional HIV entry inhibitors

| Molecule | SEQ ID NO | Sequence |
|---|---|---|
| TLT-1 | 6 | GPLGSTTWEAWDRAIAEYAARIEALLRALQEQQEKNEAALREL(GGGGS)$_7$YTSLIHSLIEESQNQQEKNEQELLELDKWASLWNWFYSSGRIVTD |
| TLT-2 | 7 | GPLGSTTWEAWDRAIAEYAARIEALLRALQEQQEKNEAALREL(GGGGS)$_7$YTSLIHSLIEESQNQQEKNEQELLELDKWASLWNWFNSSGRIVTD |
| TLT-3 | 8 | GPLGSTTWEAWDRAIAEYAARIEALLRALQEQQEKNEAALREL(GGGGS)$_6$YTSLIHSLIEESQNQQEKNEQELLELDKWASLWNWF |
| TLT-4 | 24 | GPLGSTTWEAWDRAIAEYAARIEALLRALQEQQEKNEAALREL(GGGGS)$_7$YTSLIHSLIEESQNQQEKNEQELLELDKWASLWNWF |
| TLT-5 | 25 | TTWEAWDRAIAEYAARIEALLRALQEQQEKNEAALREL(GGGGS)$_7$YTSLIHSLIEESQNQQEKNEQELLELDKWASLWNWF |
| TLT-6 | 26 | TTWEAWDRAIAEYAARIEALLRALQEQQEKNEAALREL(GGGGS)$_6$YTSLIHSLIEESQNQQEKNEQELLELDKWASLWNWF |
| TLT-7 | 27 | TTWEAWDRAIAEYAARIEALLRALQEQQEKNEAALREL(GGGGS)$_5$YTSLIHSLIEESQNQQEKNEQELLELDKWASLWNWF |
| TLT-8 | 28 | TTWEAWDRAIAEYAARIEALLRALQEQQEKNEAALREL(GGGGS)$_4$YTSLIHSLIEESQNQQEKNEQELLELDKWASLWNWF |
| TLT-9 | 29 | WMEWDREINNYTSLIHSLIEESQNQQEKNEQELL(GGGGS)$_7$YTSLIHSLIEESQNQQEKNEQELLELDKWASLWNWF |
| TLT-10 | 30 | WMEWDREINNYTSLIHSLIEESQNQQEKNEQELLEL(GGGGS)$_7$YTSLIHSLIEESQNQQEKNEQELLELDKWASLWNWF |
| TLT-11 | 31 | TTWMEWDREINNYTSLIHSLIEESQNQQEKNEQELLEL(GGGGS)$_7$YTSLIHSLIEESQNQQEKNEQELLELDKWASLWNWF |
| TLT-12 | 32 | TTWMEWDREINNYTSLIHSLIEESQNQQEKNEQELLEL(GGGGS)$_7$HSLIEESQNQQEKNEQELLELDKWASLWNWFNITNW |
| TLT-13 | 33 | TTWMEWDREINNYTSLIHSLIEESQNQQEKNEQELLEL(GGGGS)$_7$EEYTKKIEEYTKKIEEYTKKIEEYTKKIWASLWNWF |
| TLT-14 | 34 | TTWMEWDREINNYTSLIHSLIEESQNQQEKNEQELLEL(GGGGS)$_7$EELAKKAEELAKKAEELAKKAEELAKKAWASLWNWF |

The amino acid residues for the disclosed molecules include conservative natural amino acid substitutions. For example, conservative amino acid changes may be made, which although they alter the primary sequence of the protein or peptide, do not normally alter its function. Conservative amino acid substitutions typically include substitutions within the following groups: glycine and alanine; valine, isoleucine and leucine; aspartic acid and glutamic acid; asparagine and glutamine; serine and threonine; lysine and arginine; and phenylalanine and tyrosine.

Additionally, substitutions for non-natural amino acids are within the scope of the disclosed bifunctional peptides. Non-natural amino acids include, but are not limited to, D-amino acids, 6-Aminohexanoic acid, H-3-Nitro-Tyr-OH, 1-(Fmoc-amino)-cyclopentanecarboxylic acid, 4-Amino-piperidine-4-carboxylic acid, 11-(Boc-amino)-undecanoic acid, 7-Amino-4-methylcoumarin, 1-Boc-4-(Fmoc-amino)-piperidine-4-carboxylic acid, 1-Fmoc-4-(Fmoc-amino)-piperidine-4-carboxylic acid, (RS)-3-Amino-3-(3-pyridyl)-propionic acid, Bpoc-Ala-OH, H-Homoarg-OH, 3-Maleimido-propionic acid, Fmoc-4-(neopentyloxysulfonyl)-Abu-OH, Boc-α-amino-DL-Gly (Fmoc)-OH, Fmoc-α-allyl-DL-Gly-OH, Boc-Homocys(Trt)-OH, Boc-D-Homocys(Trt)-OH, Boc-Homophe-OH, H-Homophe-OH, H-DL-Isoser-OH, 4-Amino-3-(2,2-dimethoxy-ethyl)-phenol, Fmoc-α-amino-D-Gly(Boc)-OH, H-D-Pra-OH, Fmoc-Aib-OH, Statine Boc-phenylstatine, H-Ser(Bzl)-OH, H-Cys(Bzl)-OH, and Fmoc-N-Me-Val-OH.

In one embodiment disclosed herein, the pocket-binding domain comprises amino acids 628-635 (WMEWDREI; SEQ ID NO:9) of the CHR region of gp41 of HIV-1 strain HXB-2. In other embodiments the PBD comprises the corresponding amino acids of the CHR region of GP41 of any HIV-1 strain, any HIV-2 strain or any simian immunodeficiency virus (SIV) strain. In another embodiment, one to three residues of the PBD are replaced by other natural amino acids. In yet another embodiment, one to three residues of the PBD are replaced by non-natural amino acids.

In one embodiment disclosed herein, the HR-binding domain comprises amino acids 636-665 (NNYTSLIHSLIEESQNQQEKNEQELLELDK; SEQ ID NO:10) of the CHR region of gp41 of HIV-1 strain HXB-2. In other embodiments the HBD comprises the corresponding amino acids of the CHR region of GP41 of any HIV-1 strain, any HIV-2 strain or any SIV strain. In another embodiment, one to ten residues of the HBD are replaced by other natural amino acids. In yet another embodiment, one to ten residues of the HBD are replaced by non-natural amino acids.

In one embodiment disclosed herein, the tryptophan-rich domain comprises amino acids 666-673 (WASLWNWF; SEQ ID NO:21) of the CHR region of gp41 of HIV-1 strain HXB-2. In other embodiments the TRD comprises the corresponding amino acids of the CHR region of GP41 of any HIV-1 strain, any HIV-2 strain or any SIV strain. In another embodiment, one three residues of the TRD are replaced by other natural amino acids. In yet another embodiment, one to three residues of the TRD are replaced by non-natural amino acids.

The present disclosure is also directed to pharmaceutical compositions comprising the above-described bifunctional peptides that can inhibit HIV entry into a target cell, in a pharmaceutically acceptable carrier.

Dosages and desired drug concentrations of the disclosed pharmaceutical compositions may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mardenti, J. and Chappell, W. "The use of interspecies scaling in toxicokinetics" In Toxicokinetics and New Drug Development, Yacobi et al, Eds., Pergamon Press, New York 1989, pp. 42-96. The term "therapeutically effective" amount as used herein refers to the amount needed to perform the particular treatment for a disease such as, for example, an infectious disease. "Treatment" refers to both therapeutic treatment and prophylactic or preventative measures, wherein the object is to prevent or slow down (lessen) the targeted pathologic condition or disease. Those in need of treatment include those already with the disease as well as those prone to have the disease or those in whom the disease is to be prevented. In one embodiment, the disease is present. In another embodiment, the life of a cell or an individual is prolonged due to the methods described herein.

The above-described compounds can be formulated without undue experimentation for administration to a mammal, including humans, as appropriate for the particular application. Additionally, proper dosages of the compositions can be determined without undue experimentation using standard dose-response protocols.

Accordingly, the compositions designed for oral, nasal, lingual, sublingual, buccal and intrabuccal administration can be made without undue experimentation by means well known in the art, for example with an inert diluent or with an pharmaceutically acceptable carrier. The compositions are enclosed in gelatin capsules or compressed into tablets. For the purpose of oral therapeutic administration, the pharmaceutical compositions may be incorporated with excipients and used in the form of tablets, troches, capsules, elixirs, suspensions, syrups, wafers, chewing gums and the like. A "pharmaceutically acceptable carrier" means any of the standard pharmaceutical carriers. Examples of suitable carriers are well known in the art and may include but are not limited to any of the standard pharmaceutical carriers like phosphate buffered saline solutions, phosphate buffered saline containing Polysorb 80, water, emulsions such as oil/water emulsion, and various types of wetting agents. Other carriers may also include sterile solutions, tablets, coated tablets, and capsules. Typically such carriers contain excipients like starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

Tablets, pills, capsules, troches and the like may also contain binders, excipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, cornstarch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and nontoxic in the amounts used.

The compounds can easily be administered parenterally such as for example, by intravenous, intramuscular, intrathecal or subcutaneous injection. Parenteral administration can be accomplished by incorporating the compounds into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the compound, in a pharmaceutical composition, into the rectum or large intestine. This can be accomplished using suppositories, enemas, gels, creams, tablets, and the like. Suppository formulations can easily be made by methods known in the art. Similarly, vaginal administration forms comprising suppositories, gels, douches, creams, tablet, rings and the like can be formulated. The composition may be intended for rectal or vaginal administration, in the form, e.g., of a suppository which will melt in the rectum and release the drug. The composition for rectal or vaginal administration may contain an oleaginous base as a suitable nonirritating excipient. Such bases include, without limitation, lanolin, cocoa butter and polyethylene glycol. Low-melting waxes are preferred for the preparation of a suppository, where mixtures of fatty acid glycerides and/or cocoa butter are suitable waxes. The waxes may be melted, and the cyclohexylamine compound is dispersed homogeneously therein by stirring. The molten homogeneous mixture is then poured into convenient sized molds, allowed to cool and thereby solidify.

The disclosed composition intended for topical administration may suitably comprise a solution, emulsion, ointment, cream or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration.

Transdermal administration includes percutaneous absorption of the composition through the skin. Transdermal formulations include patches, iontophoresis devices, ointments, creams, gels, salves and the like.

The composition may include various materials which modify the physical form of a solid or liquid dosage unit. For example, the composition may include materials that form a coating shell around the active ingredients. The materials which form the coating shell are typically inert, and may be selected from, for example, sugar, shellac, and other enteric coating agents. Alternatively, the active ingredients may be encased in a gelatin capsule or cachet.

The bifunctional molecule compositions of the present disclosure may be administered in a therapeutically effective amount, according to an appropriate dosing regiment. As understood by a skilled artisan, the exact amount required may vary from subject to subject, depending on the subject's species, age and general condition, the severity of the infection, the particular agent(s) and the mode of administration. In some embodiments, about 0.001 mg/kg to about 50 mg/kg, of the composition based on the subject's body weight is administered, one or more times a day, to obtain the desired therapeutic effect. In other embodiments, about 1 mg/kg to about 25 mg/kg, of the composition based on the subject's body weight is administered, one or more times a day, to obtain the desired therapeutic effect.

The total daily dosage of the compositions will be determined by the attending physician within the scope of sound medical judgment. The specific therapeutically effective dose level for any particular patient or subject will depend upon a variety of factors including the disorder being treated and the severity of the disorder; the activity of the specific compound employed; the specific composition employed; the age, body weight, general health, sex and diet of the patient or subject; the time of administration, route of administration, and rate of excretion of the specific compound employed; the duration of the treatment; drugs used in combination or coincidental with the specific compound employed, and other factors well known in the medical arts.

The disclosed compositions may also be employed in combination therapies. That is, the compositions presently disclosed can be administered concurrently with, prior to, or subsequent to, one or more other desired compositions, therapeutics, treatments or medical procedures. The particular combination of therapies administered will be determined by the attending physician and will take into account compatibility of the treatments and the desired therapeutic effect to be achieved. It will be appreciated that therapeutically active agents utilized in combination may be administered together in a single composition, treatment or procedure, or alternatively may be administered separately.

For example, the disclosed compositions may be administered in combination with one or more other HIV inhibitors including, for example, but not limited to, one or more nucleoside/nucleotide reverse transcriptase inhibitors (NRTIs), non-nucleoside reverse transcriptase inhibitors (NNRTIs), protease inhibitors (PIs), fusion inhibitors, integrase inhibitors, chemokine receptor (CXCR4, CCR5) inhibitors and/or hydroxyurea.

Nucleoside reverse transcriptase inhibitors, include but are not limited to, Abacavir (ABC; Ziagen®), didanosine (dideoxyinosine (ddI); Videx®), lamivudine (3TC; Epivir®), stavudine (d4T; Zerit®, Zerit XR®), zalcitabine (dideoxycytidine (ddC); Hivid®), zidovudine (ZDV, formerly known as azidothymidine (AZT); Retrovir®), abacavir, zidovudine, and lamivudine (Trizivir®), zidovudine and lamivudine (Combivir®), and emtricitabine (Emtriva®). Nucleotide reverse transcriptase inhibitors include tenofovir disoproxil fumarate (Viread®). Non-nucleoside reverse transcriptase inhibitors for HIV include, but are not limited to, nevirapine (Viramune®), delavirdine mesylate (Rescriptor®), and efavirenz (Sustiva®).

Protease inhibitors (PIs) include amprenavir (Agenerase®), saquinavir mesylate (Fortovase®, Invirase®), ritonavir (Norvir®), indinavir sulfate (Crixivan®), nelfmavir mesylate (Viracept®), lopinavir and ritonavir (Kaletra®), atazanavir (Reyataz®), and fosamprenavir (Lexiva®). Atazanavir and fosamprenavir (Lexiva) are new protease inhibitors that were recently approved by the U.S. Food and Drug Administration for treating HIV-1 infection (see atazanavir (Reyataz) and emtricitabine (Emtriva) for HIV infection, Medical Letter on Drugs and Therapeutics, available online at www.medletter.com; U.S. Department of Health and Human Services (2003). Guidelines for the Use of Antiretroviral Agents in HIV-infected Adults and Adolescents; available online at aidsinfo.nih.gov/guidelines.

A fusion/entry inhibitor attaches to the outside of a CD4+ cell (a type of white blood cell) or coreceptors such as CCR5 and CXCR4 or to the viral membrane proteins, such as gp41 and gp120. Fusion/entry inhibitors prevent fusion between the virus and the cell from occurring or entry of the virus to the cells and therefore, prevent HIV infection and multiplication. Fusion/entry inhibitors include, but are not limited to, enfuvirtide (Fuzeon®) and maraviroc (Selzentry®, Pfizer).

An integrase inhibitor blocks the action of integrase, preventing HIV-1 genetic material from integrating into the host DNA, and thereby stopping viral replication. Integrase inhibitors include, but are not limited to, raltegravir (Isentress®, Merck); and elvitegravir (GS 9137, Gilead Sciences).

Alternatively or additionally, the compositions disclosed herein may be administered in combination with one or more anti-infective agents (e.g., antibiotics, etc.), pain relievers, or other agents intended to address symptoms of one or more diseases, disorders, or conditions commonly found in immunocompromised individuals but not directly caused by HIV.

EXAMPLES

The following examples are included to demonstrate embodiments of the disclosed bifunctional molecules. It should be appreciated by those of skill in the art that the techniques disclosed in the examples which follow represent techniques discovered by the inventors to function well in the practice of the present disclosure, and thus can be considered to constitute preferred modes for its practice. However, those of ordinary skill in the art should, in light of the present disclosure, appreciate that many changes can be made in the specific embodiments which are disclosed and still obtain a like or similar result without departing from the spirit and scope of the invention.

Example 1

Expression, Purification and Characterization of the Bifunctional Molecule TLT-1

To create the expression plasmid for the exemplary bifunctional molecule TLT-1, pTLT-1, DNA fragments encoding T1144, the 35-mer linker (GGGGS), SEQ ID NO: 40), and T20 were linked together by three-step overlapping PCR. Firstly, the T1144, L35 and T20 DNA fragments were generated by overlapping PCR using the corresponding primer pairs as described in Table 4. Secondly, the DNA fragments coding for L35 and T20 were linked by overlapping PCR with the primers FL35 and RT20. Thirdly, the two DNA fragments encoding T1144 and L35-T20 were linked by overlapping PCR with the primers FT1144 and RT20. Finally, the amplified DNA fragment coding for T1144-L35-T20 was digested by BamHI and XhoI and inserted into the expression vector pGEX-6p-1 to generate the pTLT-1 plasmid.

TABLE 4

Primers used for constructing the expression vector, pTLT-1

| DNA fragment encoding | Primer | Sequence (5' to 3')* |
|---|---|---|
| T1144 | FT1144 | CCGGGGATCCACGACCTGGGAAGCATGGGAC AGAGCTATTGCTGAATACGCAGCTAGGATAG AAGCTTTACTCAGAGCTTTA SEQ ID NO:47 |
|  | RT1144 | ACTTCCTCCTCCTCCTAATTCCCTTAAGGCT GCTTCATTCTTTTCTTGCTGTTCTTGTAAAG CTCTGAGTAAAGC SEQ ID NO:48 |
| 35-mer linker | FL35 | GGAGGAGGAGGAAGTGGCGGCGGCGGCTCGG GTGGTGGTGGTTCTGGAGGTGGCGGTAGCGG AGGTGGAGGTAGTGGAGGC SEQ ID NO:49 |
|  | RL35 | GCTACCTCCGCCTCCCGAACCTCCGCCTCCA CTACCTCCACCTCCGCTACCGCCACCTCCAG AACCACCACCACCCGAG SEQ ID NO:50 |
| T20 | FT20 | GGAGGCGGAGGTAGCTACACAAGCTTAATAC ACTCCTTAATTGAAGAATCGCAAAACCAGCA AGAAAAGAATGAACAA SEQ ID NO:51 |
|  | RT20 | CCGCTCGAGTTAAAACCAATTCCACAAACTT GCCCATTTATCTAATTCCAATAATTCTTGTT CATTCTTTTC SEQ ID NO:52 |

*The sequences underlined are restriction enzyme sites used for clone gene into vector pGEX-6p-1.

To express the TLT-1 fusion peptide, E. coli strain Rosetta 2 (DE3) pLysS (Novagen) was transformed with pTLT-1, cultured at 37° C. to $OD_{600}$=0.4, then induced for 4 hr. The cells were harvested and lysed by sonication in presence of protease inhibitor mixture (Roche). After centrifugation, supernatants containing the TLT-1-GST fusion protein were collected. Then, TLT-1-GST was purified using a Glutathione-Sepharose 4B affinity column and cleaved with PreScission™ Protease (GE Healthcare) to release the bifunctional proteins from the GST. The bifunctional proteins were then purified by fast protein liquid chromatography (FPLC) and analyzed by SDS-PAGE.

Figure 3:
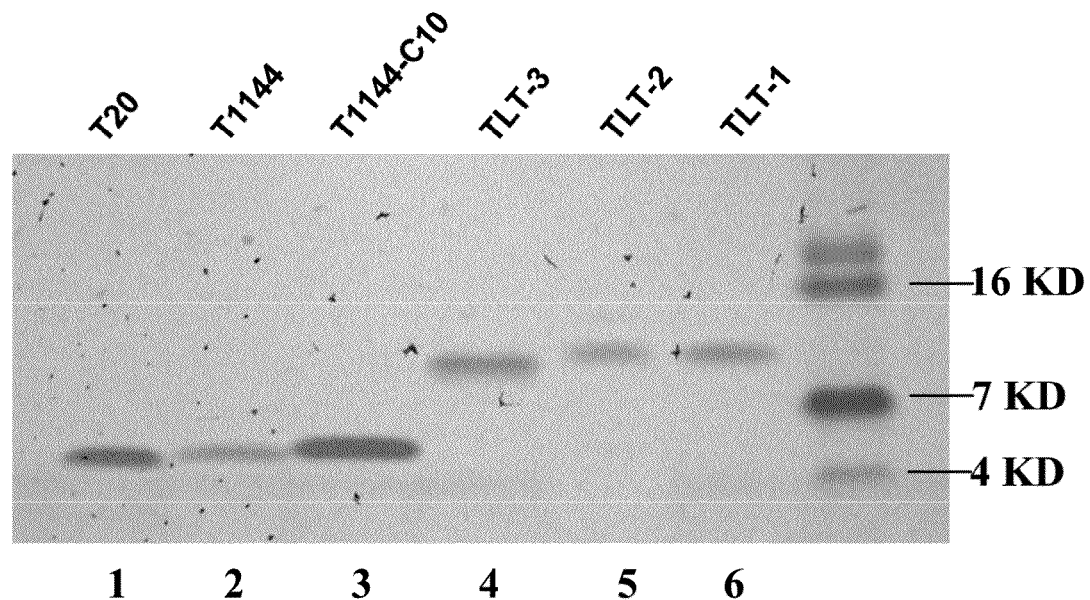
FIG. 3 depicts SDS-PAGE analysis of the purified HIV entry inhibitors.

The TLT-1 exemplary bifunctional molecule consisted of a 38-mer of T1144 (TTWEAWDRAIAEYAARIEALL-RALQEQQEKNEAALREL; SEQ ID NO:4), a 35-mer of linker [(GGGGS)$_7$; SEQ ID NO:40] and a 36-mer of T20 (YTSLIHSLIEESQNQQEKN EQELLELDKWASL-WNWF; SEQ ID NO:2). Sequencing the resultant vectors indicated that three different vectors were generated. All three had five extra amino acid residues (GPLGS) at the N-terminus. Two plasmids displayed that their protein sequences also had nine extra amino acid residues (YSSGRIVTD [SEQ ID NO:53] or NSSGRIVTD [SEQ ID NO:42]) at the C-termini. One plasmid did not have the extra nine extra amino acid residues at the C-terminus, but did include a 30-mer linker (SEQ ID NO: 39), rather than the expected 35-mer linker. These three plasmids demonstrate different expression efficiency in E. coli, i.e., the vector which had the TLT-1 gene with the 30-mer linker was poorly expressed in bacteria while the other two with nine additional amino acids at C-termini were better expressed. The plasmid with YSSGRIVTD was selected as a representative bifunctional molecule for further studies. The purified bifunctional peptide demonstrated a molecular weight of about 12 kD by SDS-PAGE (FIG. 3).

Example 2

Anti-HIV Activity of TLT-1

TLT-1 was highly active in inhibiting HIV-1-mediated cell-cell fusion and infection by laboratory-adapted and primary HIV-1 strains.

Figure 4:
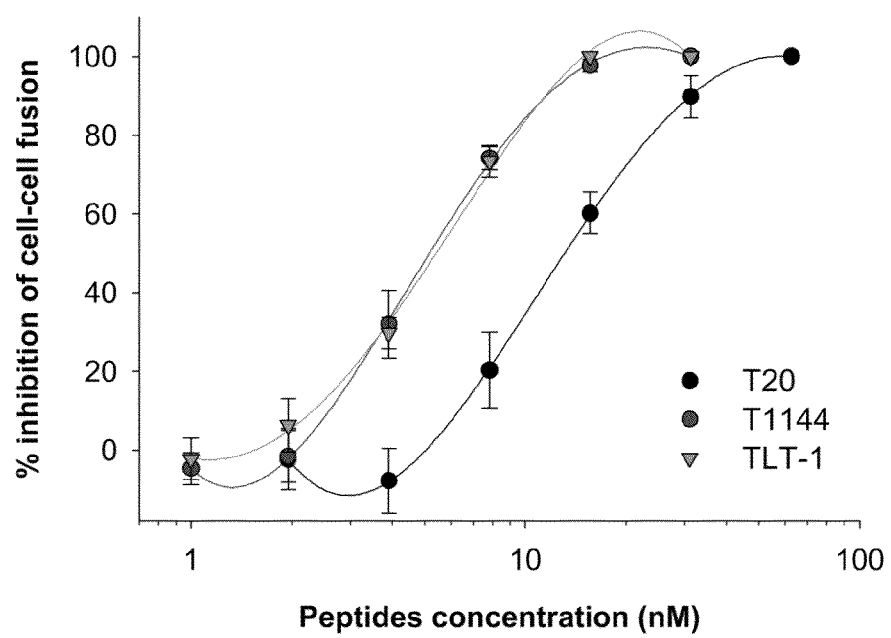
FIG. 4 depicts the inhibition by the HIV entry inhibitors of HIV-1-mediated cell-cell fusion as determined by dye-transfer assay.

HIV-1-mediated cell-cell fusion was determined by a dye transfer assay (Lu H et al. J Virol Methods 107:155-161, 2003) using Calcein AM-labeled HIV-1IIIB chronically infected H9 (H9/HIV-1 IIIB) cells as effector cells and MT-2 cells as target cells. The percent inhibition of cell-cell fusion by the chimeras was calculated, and 50% inhibitory concentration (IC50) was calculated using the CalcuSyn software. As shown in FIG. 4 and Table 5, TLT-1 was highly effective in inhibiting HIV-1-mediated cell-cell fusion with $IC_{50}$ at low nM level, better than T20 and almost identical with T1144, currently the most potent HIV-1 fusion inhibitor.

Figure 5:
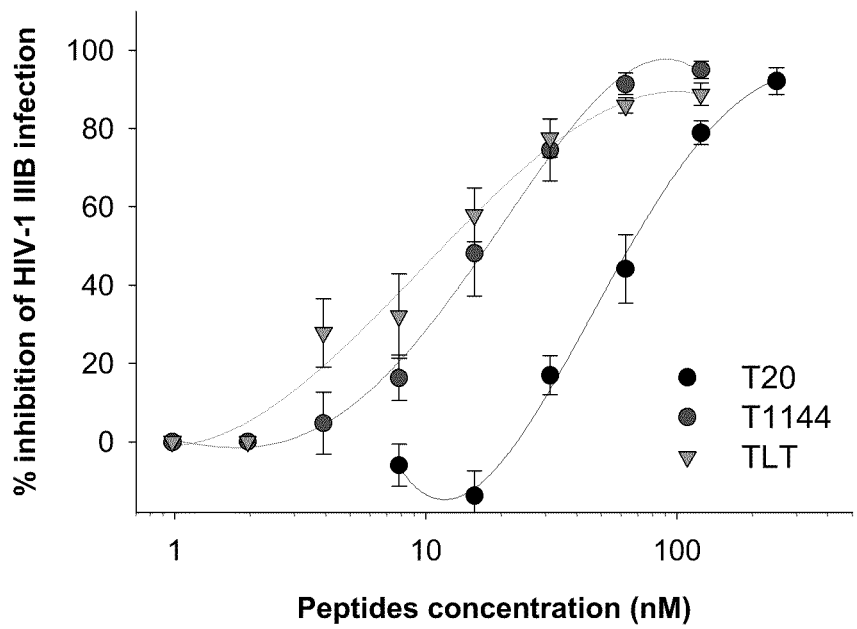
FIG. 5 depicts the inhibition by the HIV entry inhibitors of infection by a laboratory-adapted HIV-1 IIIB strain (subtype B, X4) in MT-2 cells as determined by p24 assay.

The inhibitory activity of the bifunctional molecule on HIV-1 IIIB infection was determined by ELISA for p24 production (Jiang S et al. J Exp Med 174:1557-1563, 1991). Briefly, MT-2 cells were infected with HIV-1$_{IIIB}$ at 100 TCID$_{50}$ (50% tissue culture infective dose) in RPMI 1640 medium containing 10% FBS in the presence or absence of an antigen specific antiserum or IgG antibody in serial 2-fold dilutions at 37° C. overnight. The culture supernatants were then removed and fresh media were added. On day 4 post-infection, the culture supernatants were collected and mixed with equal volumes of 5% Triton X-100 for the detection in the p24 protein ELISA. TLT-1 was also highly potent in inhibiting HIV-1 IIIB infection with $IC_{50}$ at 11 nM, more than 6-fold better than T20 (FIG. 5 and Table 5).

The inhibitory activity of the bifunctional molecule on infection by primary HIV-1 isolates 92US657 (subtypes B, X5) and 93IN101 (subtype C, X5) was determined (Jiang S et al. Antimicrob Agents Chemother 48:4349-4359, 2004). Briefly, the peripheral blood mononuclear cells (PBMCs) were isolated from the blood of healthy donors using a standard density gradient (Histopaque-1077, Sigma) centrifugation. After incubation at 37° C. for 2 hr, the nonadherent cells were collected and resuspended at 5×10$^5$/ml in RPMI 1640 medium containing 10% FBS, 5 μg of phytohemagglutinin (PHA)/ml, and 100 U of IL-2/ml, followed by incubation at 37° C. for 3 days. The PHA-stimulated cells were infected with the corresponding primary HIV-1 isolates at a multiplicity of infection (MOI) of 0.01 in the absence or presence of antisera at a serial 2-fold dilution. The supernatants were collected 7 days post-infection and tested for p24 antigen by ELISA as described above. The IC50 was calculated using the CalcuSyn

TABLE 5

Inhibitory activity of the peptides and recombinant proteins on HIV-1-mediated cell-cell fusion and HIV-1 replication

| Concentration (nM) for inhibiting | T20 | | T1144 | | T1144-C10 | | TLT-1 | | TLT-2 | | TLT-3 | |
|---|---|---|---|---|---|---|---|---|---|---|---|---|
| | $IC_{50}$ | $IC_{90}$ | $IC_{50}$ | $IC_{90}$ | $IC_{50}$ | $IC_{90}$ | $IC_{50}$ | $IC_{90}$ | $IC_{50}$ | $IC_{90}$ | $IC_{50}$ | $IC_{90}$ |
| HIV-1 IIIB-mediated cell fusion | | | | | | | | | | | | |
| | 15.9 | 25.4 | 5.2 | 10.2 | 16.8 | 49.7 | 5.1 | 7.6 | 5.0 | 7.4 | 6.2 | 14.0 |
| HIV-1 replication | | | | | | | | | | | | |
| IIIB (B, X4) | 68.1 | 211.2 | 13.0 | 65.7 | >250 | >250 | 11.0 | 84.9 | 44.6 | 177.7 | 27.1 | 186.2 |
| NL4-3$_{V38A/N42G}$* | >2,000 | >2,000 | 6.1 | 59.2 | ND | ND | 5.0 | 55.1 | 2.6 | 25.0 | 3.4 | 19.4 |
| 92US657 (B, R5)¶ | 1.7 | 13.0 | 0.3 | 5.2 | ND | ND | 1.0 | 3.3 | ND | ND | ND | ND |
| 93IN101 (B, R5)¶ | 2.7 | 6.5 | 2.5 | 13.3 | ND | ND | 5.6 | 42.6 | ND | ND | ND | ND |

Figure 6A:
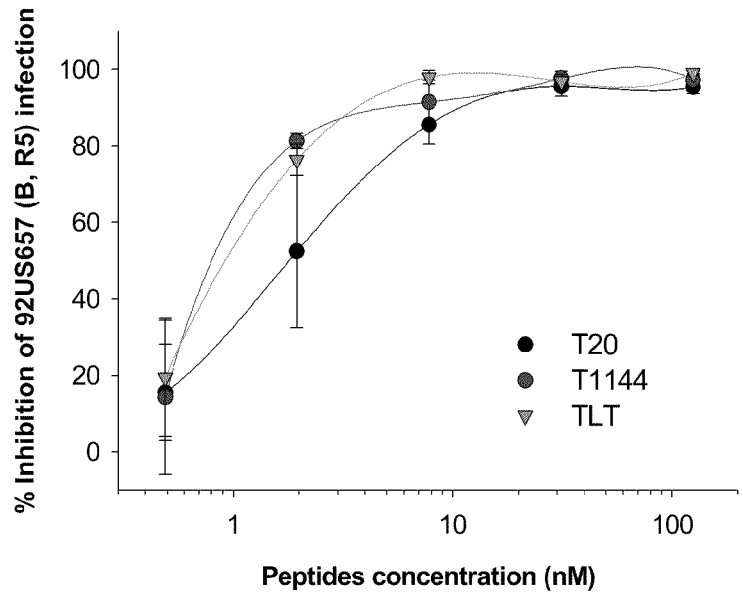
FIG. 6A—Inhibition of infection by primary HIV-1 92US657 (subtype B, R5) in PBMCs as determined by p24 assay.
Figure 6B:
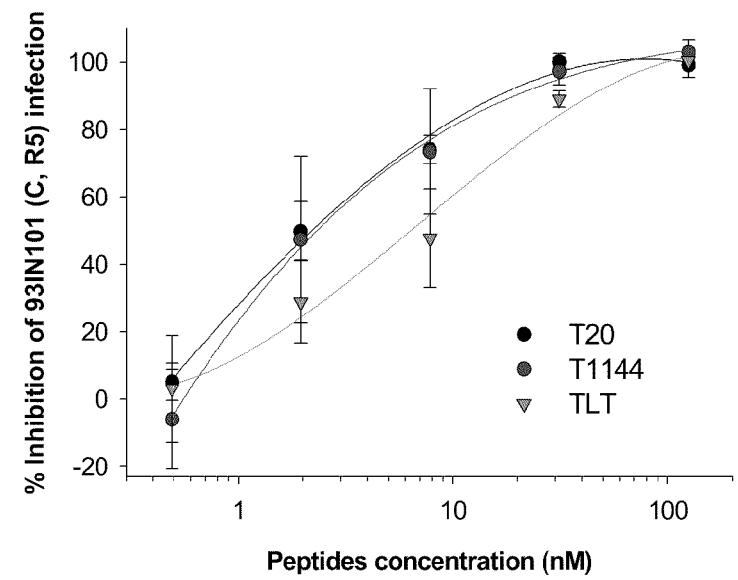
FIG. 6 depicts inhibition by HIV entry inhibitors of infection by primary HIV-1 isolates.

*T20-resistant HIV-1 strain.
¶Primary HIV-1 isolates.

software as described above. As shown in FIG. 6 and Table 5, TLT-1 significantly inhibited infection by both primary HIV-1 isolates 92US657 and 93IN101 in dose-dependent manor with $IC_{50}$ at low nM level.

Figure 7:
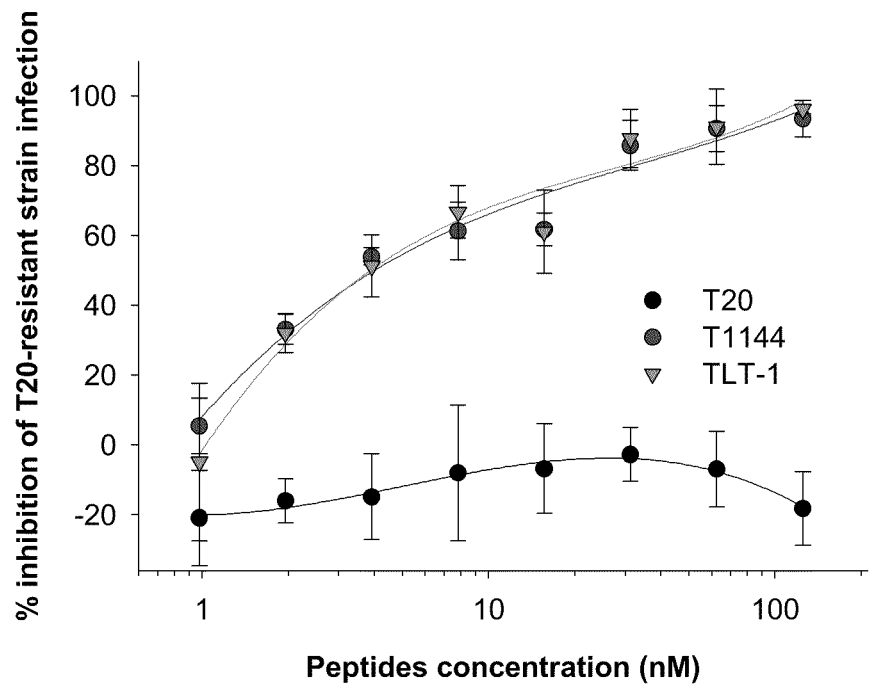
FIG. 7 depicts inhibition by HIV entry inhibitors of infection by T20 resistant HIV-1 strain, NL4-$_{3V38A/N42G}$.

The inhibitory activity of the bifunctional molecule on infection by HIV-1 NL4-3V38E/N42S (T20-resistant mutant) was determined by a luciferase activity (Neurath A R et al. BMC Infect Dis 2:6, 2002). Briefly, $2\times10^5$ or $5\times10^5$ CEMx174 5.25M7 cells were infected with HIV-1 or HIV-2, respectively, at 100 $TCID_{50}$ (50% tissue culture infective dose) in RPMI 1640 medium containing 10% FBS in the absence or presence of an antisera or purified IgG antibodies at graded concentrations overnight. On the fourth day post-infection, cells were harvested and lysed using a lysis buffer (Promega, Madison, Wis.). The luciferase activity was measured by Ultra 384 luminometer reader (Tecan) and the percent inhibition was calculated. TLT-1 was highly effective in inhibiting infection by T20-resistant strains with IC50 of 5 nM, while T20 showed no inhibition at concentration up to 2,000 nM (FIG. 7 and Table 5).

Example 3

Stability of TLT-1

Figure 8A:
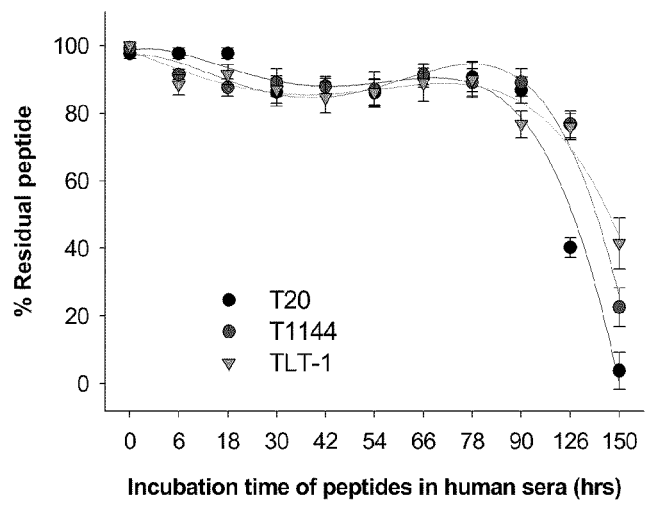
FIG. 8 depicts the stability of TLT-1 in human sera (FIG. 8A) and in PBMC cultures (FIG. 8B).
Figure 8B:
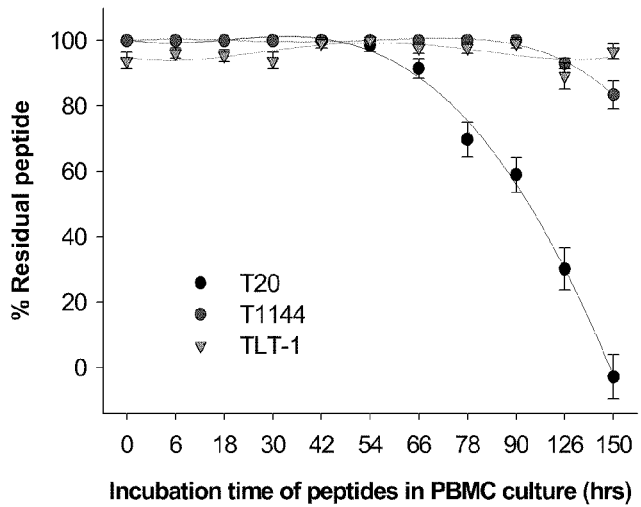

To test the in vitro stability, TLT-1, T20, or T1144 (final concentration 16 µM) was incubated at 37° C. with PBMC (in RPMI1640 containing 10% fetal bovine serum) or human serum (100%), respectively. Samples were collected at different intervals and tested for the residual concentrations of the active component using cell-cell fusion inhibition assay as described above. TLT-1 was stable in the presence of human serum and PBMC and more resistant to proteolysis than T1144 and T20. The stability of TLT-1 was first assayed in the presence of human sera and PBMC and compared with those of T20 and T1144. All three peptides tested were stable in human serum and were fully active for up to 4 days (FIG. 8A) and began lost activity thereafter; TLT-1 maintain 40% activity after 6 days, more stable than T1144 and T20, with 20% and 5% residual activity, respectively. T20 began to loose activity in PBMC in after 2 days and lost >90% of activity after 6 days incubation, while T1144 and TLT-1 showed no activity lost during the PBMC assay (FIG. 8B).

Figure 9A:
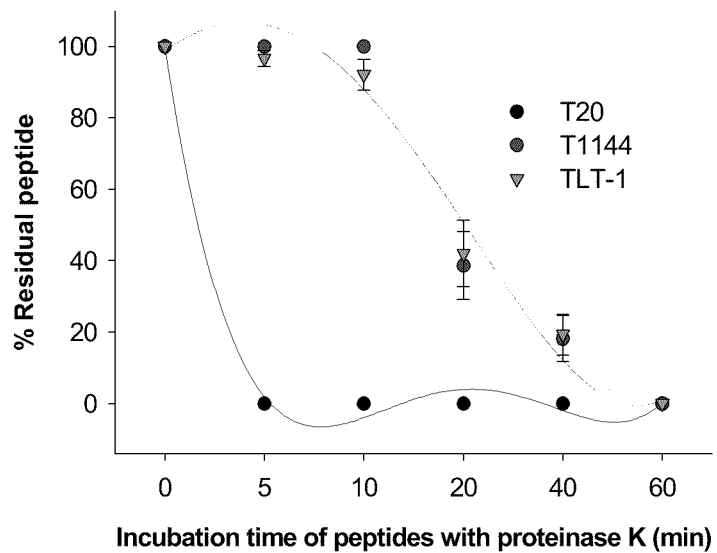
FIG. 9 depicts the sensitivity of TLT-1 to the proteolytic enzymes proteinase K (FIG. 9A) and trypsin (FIG. 9B). Each sample was tested in triplicate. Each experiment was repeated at least once and a representative set of data are presented in mean±SD.
Figure 9B:
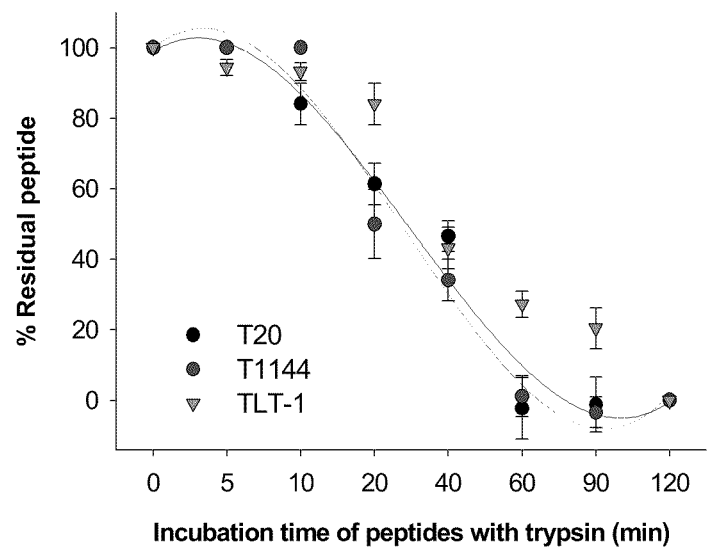

To determine resistance to proteolysis, the bifunctional protein TLT-1 and the peptides T20 and T1144 were dissolved in PBS (final concentration 4 µM) and incubated with agarose bead-immobilized proteinase K at 0.1 unit/ml or trypsin at 1 unit/ml, respectively, at 37° C. Samples were collected at various intervals, followed by measurement of the residual concentrations of the active protein or peptides using the cell fusion inhibition assay. As shown in FIG. 9, T20 totally lost its activity after 5 min treatment with proteinase K, and T1144 and TLT-1 were stable up to 15 min with proteinase K, and began to loose activity thereafter and showed similar degradation curves. All three peptides showed a time-dependent lost of activity in trypsin, while TLT-1 was more stable than T20 and T1144 with a less slope degradation curve in the trypsin test.

Example 4

The Secondary Dimensional Structure of TLT-1

TLT-1 folds into a structured protein with a high α-helix content and forms highly thermal stable complexes with N-peptide. Circular Dichroism (CD) was used to study protein and peptide secondary structure change. To determine the interaction induced secondary structure change of two peptides, the CD of the mixture was measured and those of individual peptides at the same concentration and compared the CD spectra of mixture and the sum of the spectra of two separated peptides.

Figure 10A:
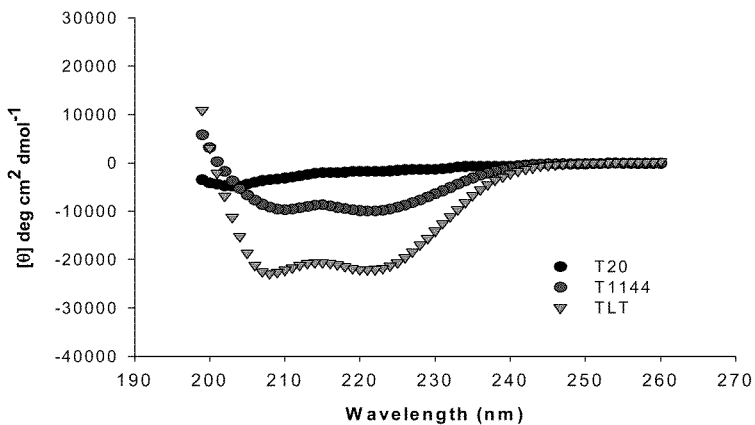
FIG. 10A—CD spectra of T1144, T20, and TLT-1.
Figure 10B:
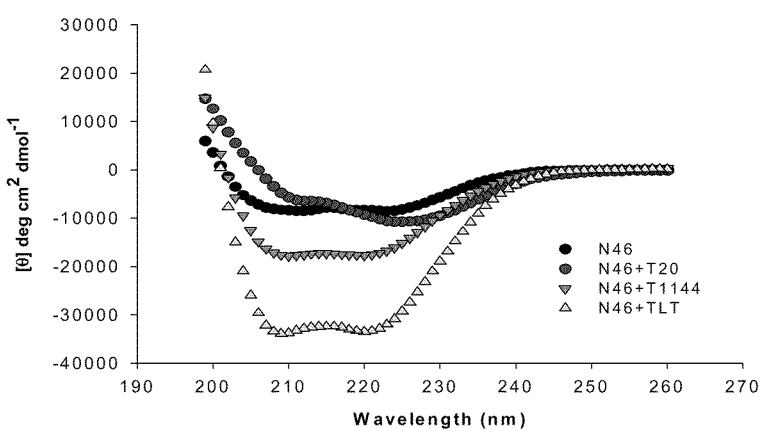
FIG. 10B—CD spectra of N46, N46+T1144, N46+T20, N46+TLT-1.

The bifunctional molecules were dissolved in 50 mM sodium phosphate and 150 mM NaCl, pH 7.2, or a mixture thereof with same molar concentration of N46 and incubated at 37° C. for 30 min. The final peptide concentration was 10 µM. The CD spectra of the individual peptides and peptide mixtures were acquired on a Jasco spectropolarimeter (Model J-715, Jasco Inc., Japan) at room temperature using a 5.0 nm band with 0.1 nm resolution, 0.1-cm path length, 4.0-s response time, and a 50 nm/min scanning speed. The spectra were corrected by subtraction of a blank corresponding to the solvent. The α-helical content was calculated from the CD signal by dividing the mean residue ellipticity at 222 nm by the value expected for 100% helix formation (33,000 degrees cm2 dmol$^{-1}$). Thermal denaturation was monitored at 222 nm by applying a thermal gradient of 2° C./min in the range of 4-98° C. To determine the reversibility, the peptide mixtures were cooled to 4° C. and kept in the CD chamber at 4° C. for 30 min, followed by monitoring of thermal denaturation as described above. T20 was unstructured in solution, while T1144 formed typical α-helical structure with calculated approximate 80% helicity in solution. TLT-1 had much higher helical content than T20 and T1144 (FIG. 10A). Consistent with previous observations, T20 could not form 6-HB with N46 while T1144 was able to interact with N46 to form stable 6-HB. Strikingly, the bifunctional molecule TLT-1 bound tightly to N46 and formed an extremely stable complex in PBS (FIG. 10B).

Figure 11:
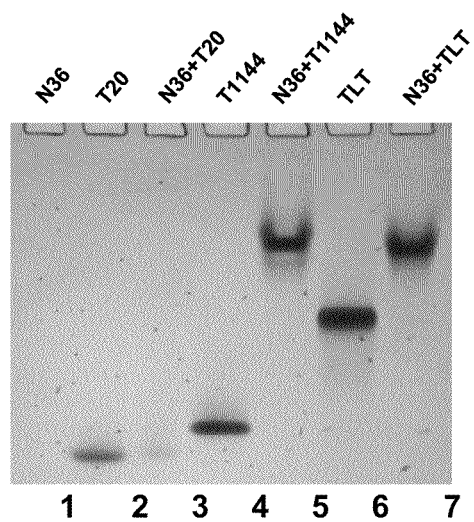
FIG. 11 depicts the native PAGE (N-PAGE) analysis of TLT-1 for formation of 6-HB with N36.

Native-PAGE (N-PAGE) was carried out to determine the 6-HB formation between the N- and C-peptides. An N-peptide (N36) was mixed with a C-peptide at a final concentration of 40 µM and incubated at 37° C. for 30 min. The mixture was loaded onto 10×1.0 cm precast 18% Tris-glycine gels (Invitrogen) at 25 µl/per well with an equal volume of Trisglycine native sample buffer (Invitrogen). Gel electrophoresis was carried out with 125 V of constant voltage at room temperature for 2 hr. The gel was then stained with Coomassie Blue and imaged with a FluorChem 8800 imaging system (Alpha Innotech Corp., San Leandro, Calif.). N-PAGE showed that like T1144, TLT-1 could form a 6-HB with N36 (FIG. 11).

Example 5

TLT-1 Inhibits 6-Helical Bundle Formation

Figure 12A:
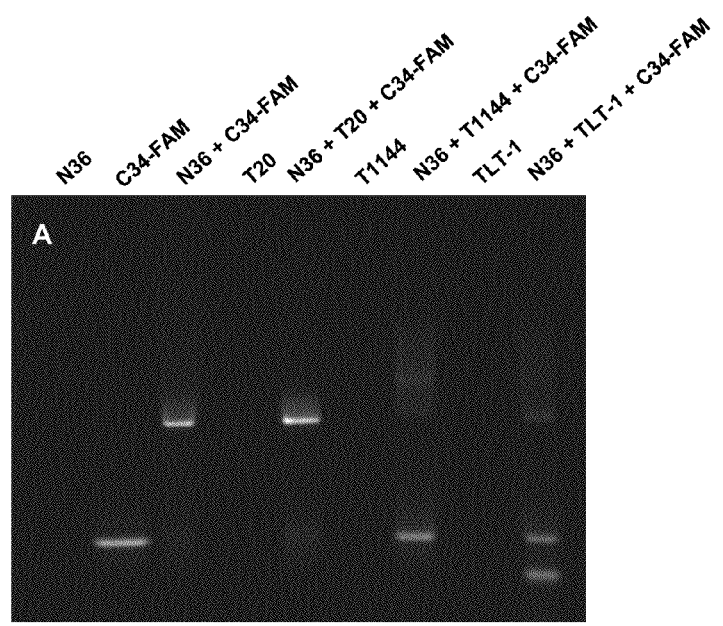
FIG. 12 depicts the inhibitory effect of TLT-1 on 6-HB formation by FN-PAGE analysis (FIG. 12A) and Coomassie blue staining of FN-PAGE gel (FIG. 12B).
Figure 12B:
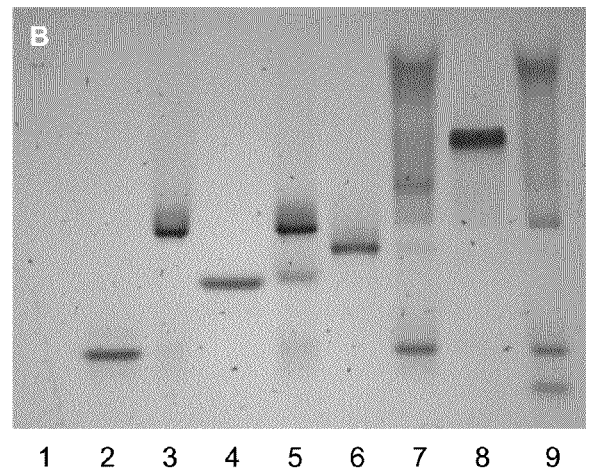

The ability of TLT-1 to prevent 6-HB formation was determined by fluorescent N-PAGE (FN-PAGE) using a fluorescent C34-FAM probe. As shown in FIG. 12, C34-FAM formed stable 6-HB with N36. The ability of T20, T1144 and TLT-1 to inhibit C34-FAM/N36 6-HB formation was also tested. T20 could not compete with C34 or N36 to prevent 6-HB formation. T1144 prevented C34-FAM/N36 6-HB formation completely by competing with C34-FAM to form a stable complex with N36. TLT-1 strongly prevented C34-FAM/N36 6-HB formation and formed a complex with N36. Interestingly, a new fluorescence band with fast shift rate was shown in the N36/TLT-1/C34-FAM mixture. The band was confirmed as a TLT-1/C34-FAM complex comprised of a mixture of C34-FAM and TLT without N36 (data not shown). The fast shift rate indicated that the TLT-1/C34-FAM folded into a compact structure and was more freely immigrating in the gel.

Example 6

TLT-1 is not Appreciably Immunogenic

Figure 13A:
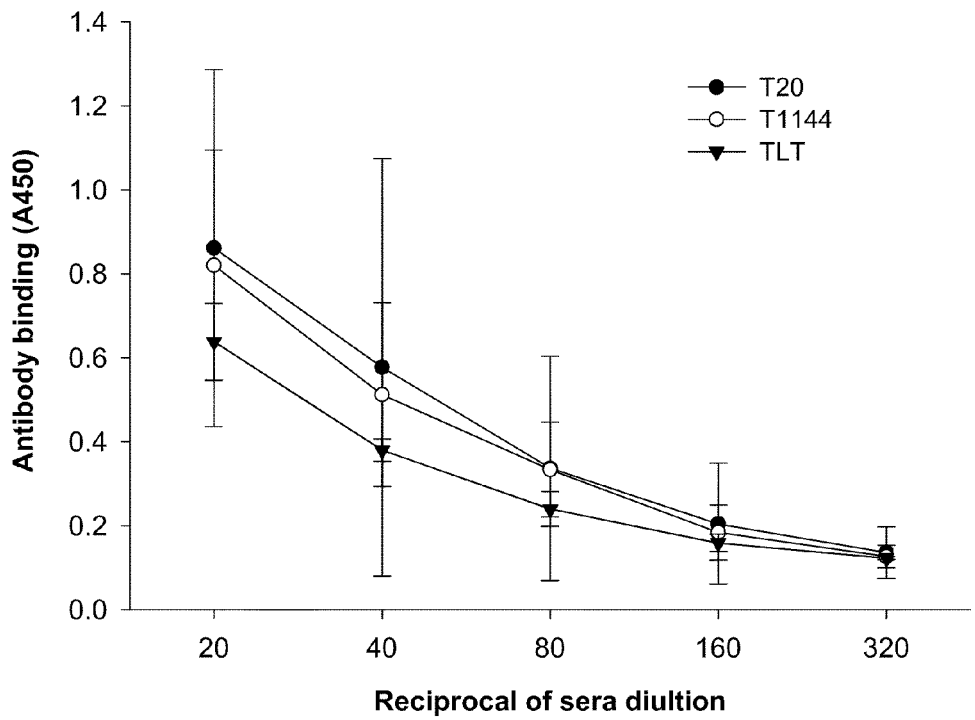
FIG. 13A depicts that TLT-1 did not induce a high titer of anti-TLT-1 antibody in animals.
Figure 13B:
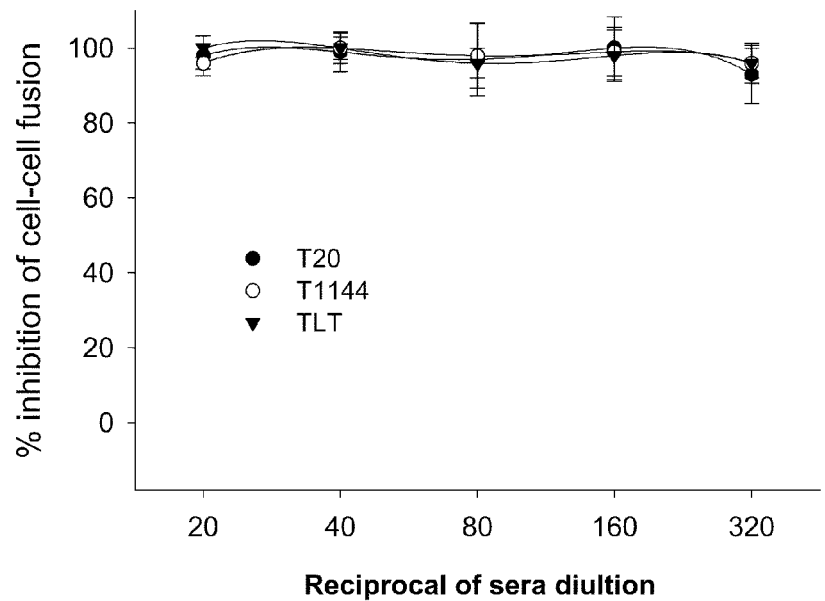
FIG. 13B depicts that the anti-HIV-1 activity of TLT-1 could not be blocked by the antibodies induced in the mice administrated with TLT-1.

TLT-1 is a well-folded protein of molecule weight around 12 kD and therefore its antigenicity was evaluated. Mice were immunized with T20, T1144 and TLT-1, boosted twice after 10 days and antibody levels were checked after 30 days. Very weak antibody responses were observed for all three peptides, and TLT-1 showed even lower immunogenicity than T20 and T1144 (FIG. 13A). None of the antisera from the mice immunized with T20, T1144 and TLT-1 showed any inhibition on the HIV-1-mediated cell-cell fusion (FIG. 13B), confirming that the weak anti-TLT-1 antibody responses in the mice administrated with TLT-1 cannot suppress the anti-HIV activity of TLT-1.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

---

What is claimed is:

1. A bifunctional protein consisting essentially of:
   a first C-terminal heptad repeat (CHR) peptide of a human immunodeficiency virus 1 (HIV-1) gp41 containing a pocket-binding domain and a heptad repeat (HR)-binding domain, wherein said first CHR peptide is directly linked to;
   a flexible linker comprising the amino acid sequence (GGGGS)$_n$, wherein n is an integer between 6 and 8 (SEQ ID NOs:39, 40 and 41), which in turn is directly linked to;
   a second CHR peptide of an HIV-1 gp41 containing a HR-binding domain and a tryptophan-rich domain.

2. The bifunctional protein of claim 1 wherein said first CHR peptide comprises the amino acid sequence selected from the group consisting of C34 (SEQ ID NO:11), C36 (SEQ ID NO:12), C38 (SEQ ID NO:3), C46 (SEQ ID NO:13), T1144 (SEQ ID NO:4), T1144-C10 (SEQ ID NO:5), sifuvirtide (SEQ ID NO:14), C35-EK (SEQ ID NO:15), CP621-652 (SEQ ID NO:16), CP32M (SEQ ID NO:17), T1249 (SEQ ID NO:18), PBD-4HR (SEQ ID NO:19), and C36B (SEQ ID NO:20).

3. The bifunctional protein of claim 1 wherein said second CHR peptide comprises the amino acid sequence selected from the group consisting of T20 (SEQ ID NO:2), T20-A (SEQ ID NO:22), and 4HR-LBD (SEQ ID NO:23).

4. The bifunctional protein of claim 1 additionally comprising the amino acid sequence YSSGRIVTD (SEQ ID NO:53) or NSSGRIVTD (SEQ ID NO:42) at the C-terminus of said bifunctional protein.

5. The bifunctional protein of claim 1 wherein said bifunctional protein comprises the amino acid sequence of GPLGSTTWEAWDRAIAEYAARIEALL-RALQEQQEKNEAALREL(GGGGS)$_7$YTSLIH-SLIEESQN QQEKNEQELLELDKWASLWNWFYSS-GRIVTD (SEQ ID NO:6).

6. The bifunctional protein of claim 1 wherein said bifunctional protein comprises the amino acid sequence of GPLGSTTWEAWDRAIAEYAARIEALL-RALQEQQEKNEAALREL(GGGGS)$_7$YTSLIH-SLIEESQN QQEKNEQELLELDKWASLWNWFNSS-GRIVTD (SEQ ID NO:7).

7. The bifunctional protein of claim 1 wherein said bifunctional protein comprises the amino acid sequence of GPLGSTTWEAWDRAIAEYAARIEALL-RALQEQQEKNEAALREL(GGGGS)$_6$YTSLIH-SLIEESQN QQEKNEQELLELDKWASLWNWF (SEQ ID NO:8).

8. The bifunctional protein of claim 1 wherein said bifunctional protein is produced by recombinant DNA technology.

9. The bifunctional protein of claim 8 wherein said bifunctional protein is produced in an expression system selected from the group consisting of bacteria, yeast, insect cells and mammalian cells.

10. The bifunctional protein of claim 9 wherein said bifunctional protein is produced in *Escherichia coli*.

11. The bifunctional protein of claim 1 wherein said bifunctional protein is synthesized on a solid or in solution.

12. The bifunctional protein of claim 1 wherein said bifunctional protein is synthesized as several separated segments and then connected together.

13. A method of inhibiting human immunodeficiency virus infection comprising: administering a bifunctional protein of claim 1 to an individual infected with the human immunodeficiency virus, thereby inhibiting entry of the virus into a target cell, and blocking infection of the target cell with the virus.

14. The bifunctional protein of claim 1 comprising the amino acid sequence of TTWEAWDRAIAEYAARIEALL-RALQEQQEKNEAALREL(GGGGS)$_7$ YTSLIH-SLIEESQNQQEKNEQELLELDKWASLWNWF (SEQ ID NO:25).

15. The bifunctional protein of claim 1 comprising the amino acid sequence of TTWMEWDREINNYTSLIH- SLIEESQNQQEKNEQELLEL(GGGGS)₇ YTSLIH-SLIEESQNQQEKNEQELLELDKWASLWNWF (SEQ ID NO:31).

16. The bifunctional protein of claim 1 comprising the amino acid sequence of TTWMEWDREINNYTSLIH-SLIEESQNQQEKNEQELLEL(GGGGS)₇ YTSLIH-SLIEESQNQQEKNEQELLELDKWASLWNWF (SEQ ID NO:33).

\* \* \* \* \*